(12) United States Patent
Kang

(10) Patent No.: US 11,484,522 B2
(45) Date of Patent: Nov. 1, 2022

(54) COMPOSITE FORMULATION AND USE THEREOF FOR PREPARING DRUGS FOR THE TREATMENT OF TUMOURS

(71) Applicant: TIANJIN MEDICAL UNIVERSITY GENERAL HOSPITAL, Tianjin (CN)

(72) Inventor: Chunsheng Kang, Tianjin (CN)

(73) Assignee: TIANJIN MEDICAL UNIVERSITY GENERAL HOSPITAL, Tianjin (CN)

( * ) Notice: Subject to any disclaimer, the term of this patent is extended or adjusted under 35 U.S.C. 154(b) by 0 days.

(21) Appl. No.: 17/273,102

(22) PCT Filed: Jan. 16, 2019

(86) PCT No.: PCT/CN2019/071841
§ 371 (c)(1),
(2) Date: Sep. 23, 2021

(87) PCT Pub. No.: WO2020/048080
PCT Pub. Date: Mar. 12, 2020

(65) Prior Publication Data
US 2022/0008375 A1     Jan. 13, 2022

(30) Foreign Application Priority Data
Sep. 3, 2018   (CN) .......................... 201811017985.3

(51) Int. Cl.
*A61K 31/343*     (2006.01)
*A61P 35/00*     (2006.01)
*A61K 31/437*     (2006.01)
*A61K 31/7105*     (2006.01)

(52) U.S. Cl.
CPC .......... *A61K 31/343* (2013.01); *A61K 31/437* (2013.01); *A61K 31/7105* (2013.01); *A61P 35/00* (2018.01)

(58) Field of Classification Search
None
See application file for complete search history.

(56) References Cited

FOREIGN PATENT DOCUMENTS

CN     109125313 A     1/2019

OTHER PUBLICATIONS

Ohgoh. Toshiharu et al. "Studies on Benzoheterocyclic Derivatives. X.Synthesis and Analgesic Action of Benzofuran Derivatives." Yakugaku Zasshi, vol. 91. No 6. Dec. 31, 1971 (Dec. 31, 1971). pp. 603-610.
(Wu. Bei et al.). "Research Progress in DZNep in Tumor Therapy" (Tumor), vol. 36. Aug. 31, 2016 (Aug. 31, 2016). pp. 938-943.

*Primary Examiner* — Brian J Davis
(74) *Attorney, Agent, or Firm* — Global IP Services; Tianhua Gu

(57) ABSTRACT

The present disclosure relates to the field of biotechnology, and in particular, to a composite formulation and the use thereof for preparing a drug for treating a tumor. The effective components of the composite formulation of the present disclosure at least comprise a compound having a structural formula shown in Formula I and an EZH2 inhibitor. In terms of the clinical application for tumours, the present disclosure finds that a low dose of the compound having the structural formula shown in Formula I can enhance the therapeutic effects of the EZH2 inhibitor DZNEP and, when used in combination, can reduce the dosage of the EZH2 inhibitor DZNEP by ⅘ whilst ensuring pharmaceutical effectiveness, being an effective combination therapeutic solution.

37 Claims, 22 Drawing Sheets

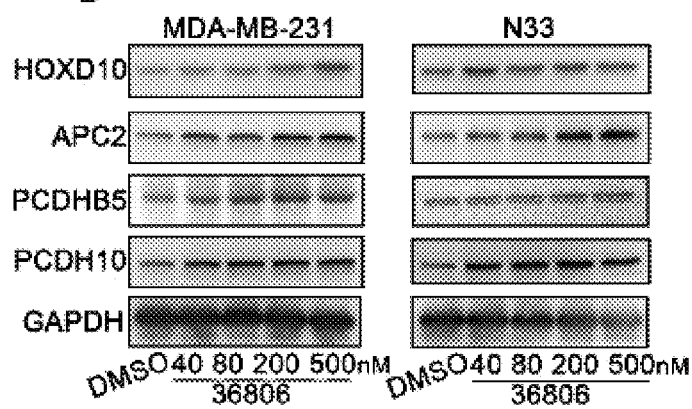
FIG. 4C
FIG. 4D
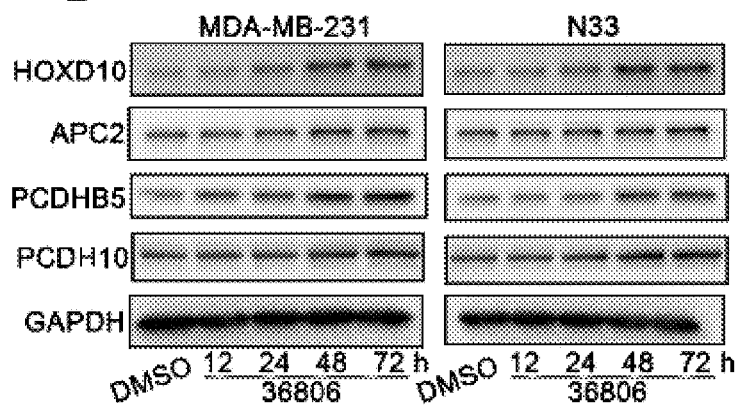
FIG. 4E

COMPOSITE FORMULATION AND USE THEREOF FOR PREPARING DRUGS FOR THE TREATMENT OF TUMOURS

CROSS REFERENCE TO RELATED PATENT APPLICATION

The present application is the US national stage of PCT/CN2019/071841 filed on Jan. 16, 2019, which claims the priority of the Chinese patent application No. 201811017985.3 filed on Sep. 3, 2018, which application is incorporated herein by reference.

TECHNICAL FIELD

The present disclosure relates to the field of biotechnology, and in particular, to a composite formulation and the use thereof for preparing drugs for the treatment of tumors.

BACKGROUND

Long nocoding RNAs (LncRNA) were initially regarded as "transcriptional noise", but they were later discovered to be related to chromosome modification and gene transcription regulation. Moreover, LncRNA plays an important role in promoting and inhibiting tumor formation and progression. A representative mechanism is transcriptional regulation, including cis-acting regulation and trans-acting regulation, connecting histone-modifying complexes to target gene loci. In tumors, HOTAIR has been studied most deeply as the star of lncRNAs. Howard Chang's group first discovered that HOTAIR can mediate the malignant invasion of breast cancer by recruiting PRC2 complexes, and revealed that the interaction between HOTAIR and PRC2 is a potential tumour therapeutic target. Later, Howard Chang's group discovered that HOTAIR can act as a scaffold, with its 5' functional domain binding to the PRC2 complex through EZH2 and its 3' functional domain connecting to the LSD1/CoREST/REST complexes. In this way, the protein inhibiting complex is brought to a target gene site for trimethylation of the lysine at position 27 of H3 histone and demethylation of the lysine at position 4 of H3 histone, thereby inhibiting gene transcription. Moreover, the binding of HOTAIR to the target gene, independent of EZH2 and PRC2, revealed the crosslinking relationship of RNA-chromatin. Later, the detailed molecular mechanism of the binding of HOTAIR's 5'domain to EZH2 was further studied, from the indispensable 300-mer region of the 5'domain to the minimum range of 89-mer (212-300) region. Although the molecular research on HOTAIR has been quite in-depth, and more and more tumors are found to be related to HOTAIR, no small molecule drugs and clinical treatments for HOTAIR have been developed so far.

SUMMARY

The present disclosure provides a composite formulation and the use thereof for preparing drugs for the treatment of tumors.

The present disclosure is achieved by the following technical solutions:

A first aspect of the present disclosure provides the use of a compound with a structural formula of Formula I in combination with an EZH2 inhibitor in the preparation of a drug for treating a tumor.

In an embodiment, the compound with a structural formula of Formula I and the EZH2 inhibitor are combined as effective components for treating tumors.

The present disclosure finds for the first time that the compound with a structural formula of Formula I can enhance the pharmacodynamic effect of the EZH2 inhibitor and reduce the dosage of the EZH2 inhibitor anti-tumor drug.

In an embodiment, the effective components of the drug for treating the tumor only include the compound with a structural formula of Formula I and the EZH2 inhibitor.

In an embodiment, in addition to the compound with a structural formula of Formula I and the EZH2 inhibitor, the effective components of the drug for treating the tumor further include other components that have therapeutic effects on a tumor.

It should be noted that the EZH2 inhibitor refers to a molecule that has an inhibitory effect on EZH2.

The inhibitory effect on EZH2 includes but is not limited to: inhibiting EZH2 activity, inhibiting the gene transcription or expression of EZH2, or inhibiting EZH2 pathway.

The EZH2 inhibitor may be siRNA, shRNA, antibody or small molecule compound.

In an embodiment, the EZH2 inhibitor is selected from DZNEP.

In an embodiment, the EZH2 inhibitor is an EZH2 interfering RNA.

The English name of DZNEP is 3-Deazaneplanocin A. The molecular formula for DZNEP is $C_{12}H_{14}N_4O_3$. The molecular weight of DZNEP is 262.269 g/mol. The CAS number of DZNEP is 120964-45-6.

The structural formula of DZNEP is

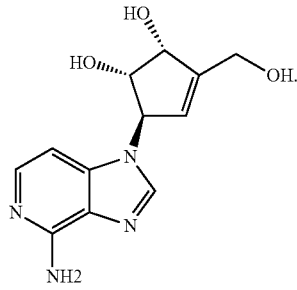

Compound with a structural formula of Formula I:

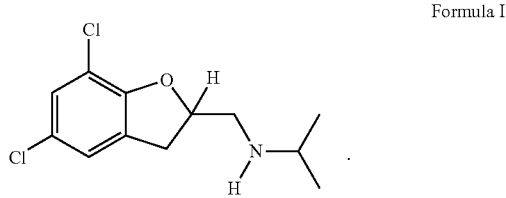 [SMILES: CC(C)NCC1Cc2cc(Cl)cc(Cl)c2O1]

Formula I

In the present disclosure, the compound with a structural formula of Formula I is also named compound 36806.

Specifically, the PubChem CID of the compound with a structural formula of Formula I is: 36806.

The chemical name of the compound with a structural formula of Formula I is: N-[(5,7-dichloro-2,3-dihydro-1-benzofuran-2-yl)methyl]propan-2-amine; AC1Q3QWB; AC1L1WF9.

In an embodiment, the tumor has high expression of HOTAIR and EZH2.

In an embodiment, the tumor is selected from breast cancer, glioma, cervical cancer, gastric cancer, melanoma, lung cancer, and liver cancer.

A second aspect of the present disclosure provides a composite formulation, and the effective components of the composite formulation at least comprise a compound having a structural formula of Formula I and an EZH2 inhibitor.

The present disclosure finds for the first time that the compound with a structural formula of Formula I can enhance the pharmacodynamic effect of the EZH2 inhibitor and reduce the dosage of the EZH2 inhibitor anti-tumor drug.

In an embodiment, the effective components of the composite formulation only include the compound with a structural formula of Formula I and the EZH2 inhibitor.

In an embodiment, in addition to the compound with a structural formula of Formula I and the EZH2 inhibitor, the effective components of the composite formulation further include other components that have therapeutic effects on a tumor.

It should be noted that the EZH2 inhibitor refers to a molecule that has an inhibitory effect on EZH2.

The inhibitory effect on EZH2 includes but is not limited to: inhibiting EZH2 activity, inhibiting the gene transcription or expression of EZH2, or inhibiting EZH2 pathway.

The EZH2 inhibitor may be siRNA, shRNA, antibody or small molecule compound.

In an embodiment, the EZH2 inhibitor is selected from DZNEP.

In an embodiment, the EZH2 inhibitor is an EZH2 interfering RNA.

The English name of DZNEP is 3-Deazaneplanocin A. The molecular formula for DZNEP is $C_{12}H_{14}N_4O_3$. The molecular weight of DZNEP is 262.269 g/mol. The CAS number of DZNEP is 120964-45-6.

The structural formula of DZNEP is

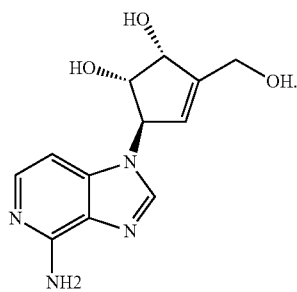

Compound with a structural formula of Formula I:

Formula I

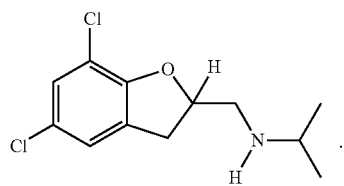

In the present disclosure, the compound with a structural formula of Formula I is also named compound 36806.

The PubChem CID of the compound with a structural formula of Formula I is:
36806.

The name of the compound with a structural formula of Formula I includes:
N-[(5,7-dichloro-2,3-dihydro-1-benzofuran-2-yl)methyl]propan-2-amine; AC1Q3QWB; AC1L1WF9.

In an embodiment, the molar ratio of the compound with a structural formula of Formula I to the EZH2 inhibitor is (20-100):(100-10000).

In an embodiment, the molar ratio of the compound with a structural formula of Formula I to the EZH2 inhibitor is (20-80):(100-10000).

In an embodiment, the molar ratio of the compound with a structural formula of Formula I to the EZH2 inhibitor is (20-40):(100-10000).

In an embodiment, the molar ratio of the compound with a structural formula of Formula I to the EZH2 inhibitor is (40-100):(100-10000).

In an embodiment, the molar ratio of the compound with a structural formula of Formula I to the EZH2 inhibitor is (40-80):(100-10000).

In an embodiment, the molar ratio of the compound with a structural formula of Formula I to the EZH2 inhibitor is (80-100):(100-10000).

In an embodiment, the molar ratio of the compound with a structural formula of Formula I to the EZH2 inhibitor is (20-100):(100-5000).

In an embodiment, the molar ratio of the compound with a structural formula of Formula I to the EZH2 inhibitor is (20-80):(100-5000).

In an embodiment, the molar ratio of the compound with a structural formula of Formula I to the EZH2 inhibitor is (20-40):(100-5000).

In an embodiment, the molar ratio of the compound with a structural formula of Formula I to the EZH2 inhibitor is (40-100):(100-5000).

In an embodiment, the molar ratio of the compound with a structural formula of Formula I to the EZH2 inhibitor is (40-80):(100-5000).

In an embodiment, the molar ratio of the compound with a structural formula of Formula I to the EZH2 inhibitor is (80-100):(100-5000).

In an embodiment, the molar ratio of the compound with a structural formula of Formula I to the EZH2 inhibitor is (20-100):(100-1000).

In an embodiment, the molar ratio of the compound with a structural formula of Formula I to the EZH2 inhibitor is (20-80):(100-1000).

In an embodiment, the molar ratio of the compound with a structural formula of Formula I to the EZH2 inhibitor is (20-40):(100-1000).

In an embodiment, the molar ratio of the compound with a structural formula of Formula I to the EZH2 inhibitor is (40-100):(100-1000).

In an embodiment, the molar ratio of the compound with a structural formula of Formula I to the EZH2 inhibitor is (40-80):(100-1000).

In an embodiment, the molar ratio of the compound with a structural formula of Formula I to the EZH2 inhibitor is (80-100):(100-1000).

In an embodiment, the molar ratio of the compound with a structural formula of Formula I to the EZH2 inhibitor is (20-100):(100-500).

In an embodiment, the molar ratio of the compound with a structural formula of Formula I to the EZH2 inhibitor is (20-100):(100-500).

In an embodiment, the molar ratio of the compound with a structural formula of Formula I to the EZH2 inhibitor is (20-80):(100-500).

In an embodiment, the molar ratio of the compound with a structural formula of Formula I to the EZH2 inhibitor is (20-40):(100-500).

In an embodiment, the molar ratio of the compound with a structural formula of Formula I to the EZH2 inhibitor is (40-100):(100-500).

In an embodiment, the molar ratio of the compound with a structural formula of Formula I to the EZH2 inhibitor is (40-80):(100-500).

In an embodiment, the molar ratio of the compound with a structural formula of Formula I to the EZH2 inhibitor is (80-100):(100-500).

In an embodiment, the molar ratio of the compound with a structural formula of Formula I to the EZH2 inhibitor is (20-100):(500-10000).

In an embodiment, the molar ratio of the compound with a structural formula of Formula I to the EZH2 inhibitor is (20-80):(500-10000).

In an embodiment, the molar ratio of the compound with a structural formula of Formula I to the EZH2 inhibitor is (20-40):(500-10000).

In an embodiment, the molar ratio of the compound with a structural formula of Formula I to the EZH2 inhibitor is (40-80):(500-10000).

In an embodiment, the molar ratio of the compound with a structural formula of Formula I to the EZH2 inhibitor is (80-100):(500-10000).

In an embodiment, the molar ratio of the compound with a structural formula of Formula I to the EZH2 inhibitor is (20-100):(500-5000).

In an embodiment, the molar ratio of the compound with a structural formula of Formula I to the EZH2 inhibitor is (20-80):(500-5000).

In an embodiment, the molar ratio of the compound with a structural formula of Formula I to the EZH2 inhibitor is (20-40):(500-5000).

In an embodiment, the molar ratio of the compound with a structural formula of Formula I to the EZH2 inhibitor is (40-80):(500-5000).

In an embodiment, the molar ratio of the compound with a structural formula of Formula I to the EZH2 inhibitor is (80-100):(500-5000).

In an embodiment, the molar ratio of the compound with a structural formula of Formula I to the EZH2 inhibitor is (20-100):(1000-10000).

In an embodiment, the molar ratio of the compound with a structural formula of Formula I to the EZH2 inhibitor is (20-80):(1000-10000).

In an embodiment, the molar ratio of the compound with a structural formula of Formula I to the EZH2 inhibitor is (20-40):(1000-10000).

In an embodiment, the molar ratio of the compound with a structural formula of Formula I to the EZH2 inhibitor is (40-80):(1000-10000).

In an embodiment, the molar ratio of the compound with a structural formula of Formula I to the EZH2 inhibitor is (80-100):(1000-10000).

In an embodiment, the molar ratio of the compound with a structural formula of Formula I to the EZH2 inhibitor is (20-100):(1000-50000).

In an embodiment, the molar ratio of the compound with a structural formula of Formula I to the EZH2 inhibitor is (20-80):(1000-50000).

In an embodiment, the molar ratio of the compound with a structural formula of Formula I to the EZH2 inhibitor is (20-40):(1000-50000).

In an embodiment, the molar ratio of the compound with a structural formula of Formula I to the EZH2 inhibitor is (40-80):(1000-50000).

In an embodiment, the molar ratio of the compound with a structural formula of Formula I to the EZH2 inhibitor is (80-100):(1000-50000).

In an embodiment, the molar ratio of the compound with a structural formula of Formula I to the EZH2 inhibitor is (20-100):(5000-10000).

In an embodiment, the molar ratio of the compound with a structural formula of Formula I to the EZH2 inhibitor is (20-80):(5000-10000).

In an embodiment, the molar ratio of the compound with a structural formula of Formula I to the EZH2 inhibitor is (20-40):(5000-10000).

In an embodiment, the molar ratio of the compound with a structural formula of Formula I to the EZH2 inhibitor is (40-80):(5000-10000).

In an embodiment, the molar ratio of the compound with a structural formula of Formula I to the EZH2 inhibitor is (80-100):(5000-10000).

In an embodiment, the molar ratio of the compound with a structural formula of Formula I to the EZH2 inhibitor is (20-100):(500-1000).

In an embodiment, the molar ratio of the compound with a structural formula of Formula I to the EZH2 inhibitor is (20-80):(500-1000).

In an embodiment, the molar ratio of the compound with a structural formula of Formula I to the EZH2 inhibitor is (20-40):(500-1000).

In an embodiment, the molar ratio of the compound with a structural formula of Formula I to the EZH2 inhibitor is (40-80):(500-1000).

In an embodiment, the molar ratio of the compound with a structural formula of Formula I to the EZH2 inhibitor is (80-100):(500-1000).

In an embodiment, the molar ratio of the compound with a structural formula of Formula I to the EZH2 inhibitor is 20:100, 20:500, 20:1000, 20:5000, 20:10000, 40:100, 40:500, 40:1000, 40:5000, 40:10000, 80:100, 80:500, 80:1000, 80:5000, 80:10000, 100:100, 100:500, 100:1000, 100:5000 or 100:10000.

In an embodiment, the molar ratio of the compound with a structural formula of Formula I to the EZH2 inhibitor is 40:1000.

Further, in addition to the effective components, the composite formulation includes one or more conventional pharmaceutically acceptable excipients.

Pharmaceutically acceptable excipients include, but are not limited to, pharmaceutically acceptable carriers, diluents, fillers, binding agents and other excipients. The therapeutically inert inorganic or organic carriers known to those skilled in the art include, but are not limited to, lactose, corn starch or derivatives thereof, talc, vegetable oils, waxes, fats, polyhydroxy compounds (such as polyethylene glycol, water, sucrose, ethanol, glycerinum and the like), various preservatives, lubricants, dispersants, and flavoring agents. Moisturizers, antioxidants, sweeteners, colorants, stabilizers, salts, buffers and the like may be added as well. The above substances are used as needed to help the stability of the formulation, help improve the activity or bio-availability of the formulation, or produce an acceptable mouth-feel or odor in the case of oral administration.

The composite formulation of the present disclosure may be prepared into any dosage form in pharmacy.

The composite formulation of the present disclosure may be prepared into oral preparations, such as capsules, tablets, dispersible tablets, buccal tablets, chewable tablets, effervescent tablets, sustained-release tablets, granules and the like. Preferably, the composite formulation of the present disclosure is prepared into capsules.

The composite formulation of the present disclosure may be administered to patients in need of treatment by oral administration, injection, sublingual administration, rectal administration, vaginal administration, transdermal administration or spray inhalation.

The dosage forms of the composite formulation of the present disclosure may be tablets, granules, capsules, pills, dropping pills, powders, lotions, syrups, stomach plates, mixtures, medicinal liquors, tinctures, buccal tablets, liquid extracts and extracts, pastes, gels, ointments, medicinal tea, lotions, coating agents, liniments, aerosols or sprays.

The composite formulation of the present disclosure may be prepared by conventional methods, such as mixing the effective components uniformly, or by mixing the effective components with corresponding excipients according to the conventional preparation methods of various preparations. The composite formulation of the present disclosure may be used in combination with other therapeutic agents.

The effective therapeutic dose of the composite formulation of the present disclosure should consider factors such as administration route and the patient's health condition, which are within the skill range of a skilled physician.

A third aspect of the present disclosure provides the use of the aforementioned composite formulation in the preparation of a drug for treating a tumor.

In an embodiment, the tumor has high expression of HOTAIR and EZH2.

In an embodiment, the tumor is selected from breast cancer, glioma, cervical cancer, gastric cancer, melanoma, lung cancer, and liver cancer.

A fourth aspect of the present disclosure provides a method for treating tumors, including administrating the aforementioned composite formulation to a subject.

The subject may be a mammal or a mammalian tumor cell. The mammals are preferably rodents, artiodactyls, perissodactyls, lagomorphs, primates, or the like. The primates are preferably monkeys, apes or humans. The tumor cell may be an in-vitro tumor cell.

The subject may be a patient suffering from a tumor or an individual expecting to treat a tumor. Alternatively, the subject may be an in-vitro tumor cell of a tumor patient or of an individual expecting to treat a tumor.

The composite formulation may be administered to the subject before, during or after the receiving of the tumor treatment.

In an embodiment, the tumor has high expression of HOTAIR and EZH2.

In an embodiment, the tumor is selected from breast cancer, glioma, cervical cancer, gastric cancer, melanoma, lung cancer, and liver cancer.

A fifth aspect of the present disclosure provides the use of the aforementioned composite formulation for the preparation of a drug having one or more of the following functions: (1) inhibiting tumor proliferation; (2) inhibiting tumor metastasis; (3) increasing the expression level of APC2; (4) reducing the expression level of beta-catenin; (5) reducing the expression level of Ki-67; (6) reducing the expression level of Vimentin.

A sixth aspect of the present disclosure provides the use of a compound with a structural formula of Formula I in the preparation of a drug for treating a tumor.

In an embodiment, the compound with a structural formula of Formula I is the only effective component or one of the effective components of the drug for treating the tumor.

In an embodiment, the tumor has high expression of HOTAIR and EZH2.

In an embodiment, the tumor is selected from breast cancer, glioma, cervical cancer, gastric cancer, melanoma, lung cancer, and liver cancer.

The present disclosure further provides a method for treating tumors by administering the compound with a structural formula of Formula I to a subject.

The subject may be a mammal or a mammalian tumor cell. The mammals are preferably rodents, artiodactyls, perissodactyls, lagomorphs, primates, or the like. The primates are preferably monkeys, apes or humans. The tumor cell may be an in-vitro tumor cell.

The subject may be a patient suffering from a tumor or an individual expecting to treat a tumor. Alternatively, the subject may be an in-vitro tumor cell of a tumor patient or of an individual expecting to treat a tumor.

The compound with a structural formula of Formula I may be administered to a subject before, during or after the receiving of the tumor treatment.

In an embodiment, the tumor has high expression of HOTAIR and EZH2.

In an embodiment, the tumor is selected from breast cancer, glioma, cervical cancer, gastric cancer, melanoma, lung cancer, and liver cancer.

A seventh aspect of the present disclosure provides the use of a compound with a structural formula of Formula I for the preparation of an interference agent interfering with the binding of HOTAIR to EZH2.

In an embodiment, the compound with a structural formula of Formula I interferes with the binding of HOTAIR 5' domain to EZH2.

An eighth aspect of the present disclosure provides the use of a compound with a structural formula of Formula I for the preparation of an interference agent interfering with the recruitment of PRC2 by HOTAIR.

A ninth aspect of the present disclosure provides the use of a compound with a structural formula of Formula I for the preparation of a reducing agent that reduces the level of H3K27me3 at a target gene site of HOTAIR.

A tenth aspect of the present disclosure provides the use of a compound with a structural formula of Formula I for the preparation of a promoter for increasing the transcription level and expression level of an HOTAIR target gene.

In an embodiment, the HOTAIR target gene is selected from HOXD10, PCDH10, PCDHB5, NLK, and APC2.

An eleventh aspect of the present disclosure provides the use of a compound with a structural formula of Formula I for the preparation of an inhibitor of WNT signal path.

A twelfth aspect of the present disclosure provides the use of a compound with a structural formula of Formula I for the preparation of an epithelial-mesenchymal transition (EMT) reversal agent for tumors.

In an embodiment, the tumor has high expression of HOTAIR and EZH2.

In an embodiment, the tumor is selected from breast cancer, glioma, cervical cancer, gastric cancer, melanoma, lung cancer, and liver cancer.

A thirteenth aspect of the present disclosure provides the use of a compound with a structural formula of Formula I for the preparation of an inhibitor of tumor proliferation, tumor invasion, and tumor metastasis. The compound with a structural formula of Formula I may be used to inhibit tumor proliferation, tumor invasion, and tumor metastasis.

In an embodiment, the tumor has high expression of HOTAIR and EZH2.

In an embodiment, the tumor is selected from breast cancer, glioma, cervical cancer, gastric cancer, melanoma, lung cancer, and liver cancer.

Compared with the existing technology, the beneficial effects of the present disclosure are:

The present disclosure uses computer simulation technology to screen for the first time small molecular compounds that can specifically interfere with the binding of HOTAIR to EZH2 based on the characteristics of the binding of HOTAIR 5' functional domain to PRC2. The compound 36806, which has a simple structure, low molecular weight and IC50, was selected, which can be processed and synthesized. In the in vivo and in vitro tests of glioma, breast cancer and other tumors, 36806 can indeed effectively interfere with the binding of HOTAIR to EZH2, affect the recruitment of PRC2 to target genes by HOTAIR, activate the transcription of target genes and increase the expression, thereby inhibiting tumor proliferation, tumor invasion and tumor metastasis, and reversing tumor EMT. In terms of the clinical application for tumours, the present disclosure finds that a low dose of 36806 can enhance the therapeutic effects of 3-Deazaneplanocin A (DZNEP) and, when used in combination, can reduce the dosage of the DZNEP by ⅘, thereby being an effective combination therapeutic solution.

BRIEF DESCRIPTION OF THE DRAWINGS

FIG. 4C: RNA levels change of target genes after treating with low-dose 36806 concentration gradient for 48 hours.

FIG. 4D: Western blot assay proved that the protein level of the target genes changed after treating with low-dose 36806 concentration gradient for 48 hours.

FIG. 4E: Western blot assay proved that the protein level of the target genes changed after treating with 40 uM of 36806 based on time gradient.

DETAILED DESCRIPTION OF THE EMBODIMENTS

Figures 1A, 1B:
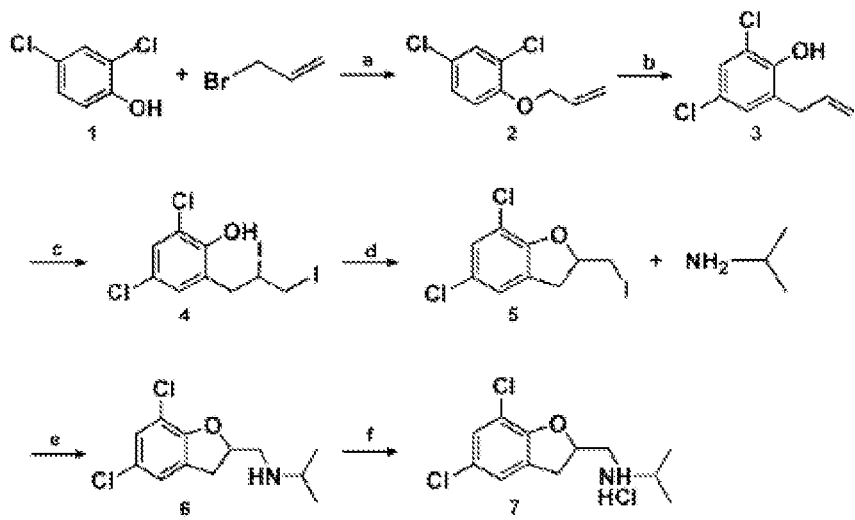
FIG. 1A: The first seven compounds in order of free energy that are selected by high-throughput screening.
FIG. 1B: An exemplary synthetic route for compound 36806.

More and more long nocoding RNA (LncRNA) are reported to play a key role in tumor formation and progression. Therefore, it is urgent to find tumor treatment methods targeting LncRNA. The present disclosure simulated the 3D structure of the HOTAIR 5'end and the 3D structure of EZH2 by using the computer. Compounds that match the binding sites were screened out from the Cancer Treatment Plan (DTP) of the National Institutes of Health (NIH), and the optimal compound "36806" was selected based on the properties of the compound and in-vitro toxicity test (IC50). Further experiments showed that the compound 36806 can specifically interfere with the binding of HOTAIR to EZH2, thereby affecting the recruitment of PRC2 to target genes by HOTAIR. Therefore, important tumor suppressor genes in the target genes are released from transcription inhibition and can be expressed, which can successfully inhibit the proliferation and metastasis of various tumors. APC2 is an important target gene of HOTAIR, which can be significantly up-regulated by the compound 36806 to degrade beta-catenin, inhibit WNT signal path, and reverse the epithelial-mesenchymal transition (EMT) of tumors. In addition, the inventors found a new combination therapy through in-vivo and in-vitro experiments, that is, a low dose of 36806 can enhance the therapeutic effects of the epigenetic therapy drug DZNEP, significantly increasing the expression of tumor suppressor genes and inhibiting the proliferation and metastasis of tumors. When used in combination with low-dose 36806, the dosage of the DZNEP can be reduced by ⅘. The present disclosure finds for the first time that in a form of a small molecule compound, by interfering with the binding of LncRNA HOTAIR to EZH2 and affecting the way that HOTAIR recruits PRC2, the malignant epigenetic regulation of tumors is altered. Further, a new drug treatment approach and a new combination therapeutic solution for tumor treatment are provided.

The embodiments of the present disclosure will be described below through exemplary embodiments. Those skilled in the art can easily understand other advantages and effects of the present disclosure according to contents disclosed by the specification. The present disclosure may also be implemented or applied through other different specific implementation modes. Various modifications or changes may be made to all details in the specification based on different points of view and applications without departing from the spirit of the present disclosure.

Before further describing the specific embodiments of the present disclosure, it is understood that the scope of the present disclosure is not limited to the specific embodiments described below. It is also to be understood that the terminology of the disclosure is used to describe the specific embodiments, instead of limiting the scope of the disclosure. In the present specification and claims, the singular forms "a", "an" and "the" include the plural forms, unless specifically stated otherwise.

When the numerical values are given by the embodiments, it is to be understood that the two endpoints of each numerical range and any one between the two may be selected unless otherwise stated. Unless otherwise defined, all technical and scientific terms used in the present disclosure have the same meaning as commonly understood by one skill in the art. In addition to the specific method, equipment and material used in the embodiments, any method, equipment and material in the existing technology similar or equivalent to the method, equipment and material mentioned in the embodiments of the present disclosure may be used to realize the invention according to the grasp of the existing technology and the record of the invention by those skilled in the art.

Unless otherwise stated, the experimental methods, detection methods, and preparation methods disclosed in the present disclosure all employ conventional techniques of molecular biology, biochemistry, chromatin structure and analysis, analytical chemistry, cell culture, recombinant DNA technology in the technical field and related fields. These techniques are well described in the existing literatures. For details, see Sambrook et al. MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; The series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, and the like.

Embodiment 1 36806 is a Simple and Easy-to-Synthesize Small Molecule Compound, which is More Sensitive in Tumors with High Expression of HOTAIR and EZH2

Among the first seven compounds screened out, the third compound 36806 was selected. As shown in FIG. 1A, the structural formula of compound 36806 is shown as Formula I,

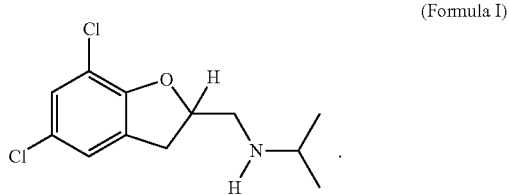 [SMILES: CC(C)NCC1Cc2cc(Cl)cc(Cl)c2O1]

(Formula I)

Figure 1C:
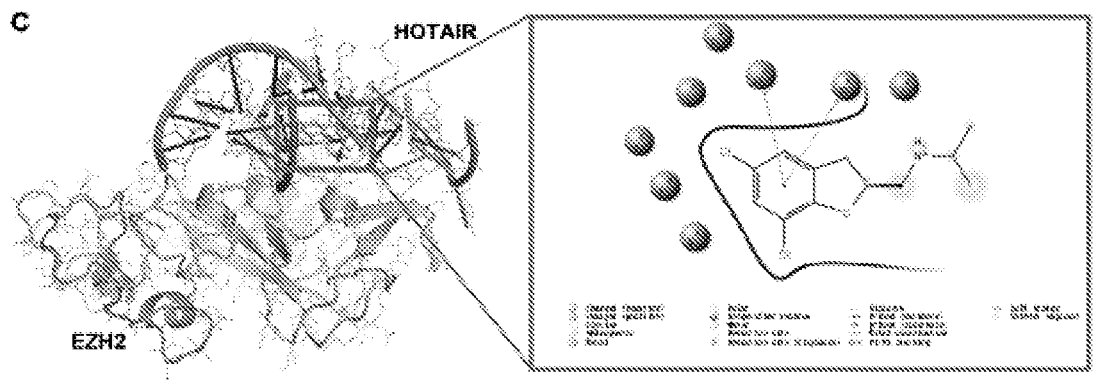
FIG. 1C: A schematic diagram showing that compound 36806 interferes with the binding of HOTAIR 5'domain to EZH2.
Figure 1D:
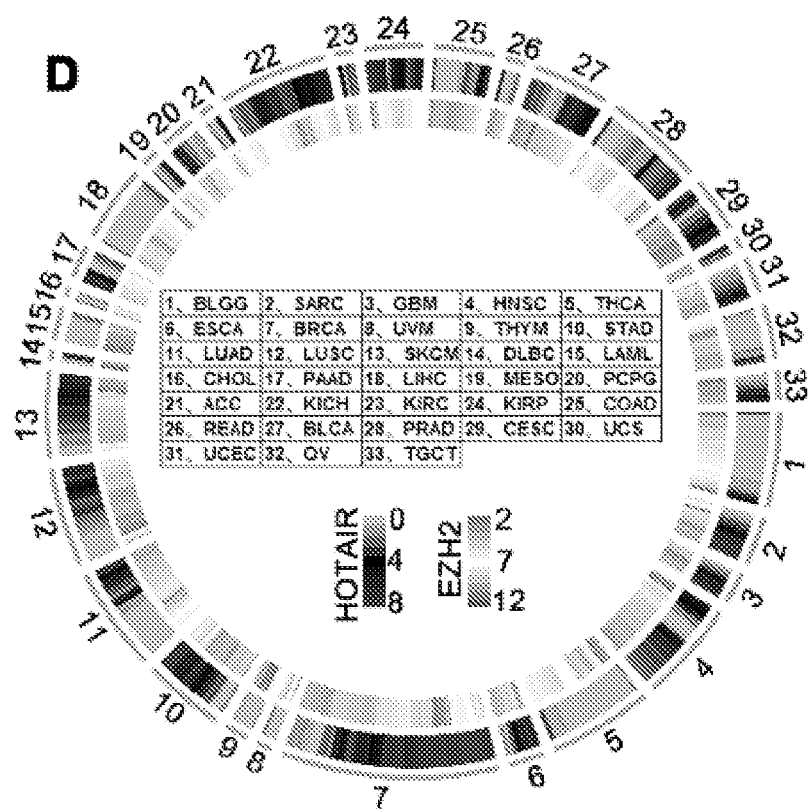
FIG. 1D: The comparison results of the expression levels of HOTAIR and EZH2 in 33 tumors in the TCGA Pancancer database.
Figure 1E:
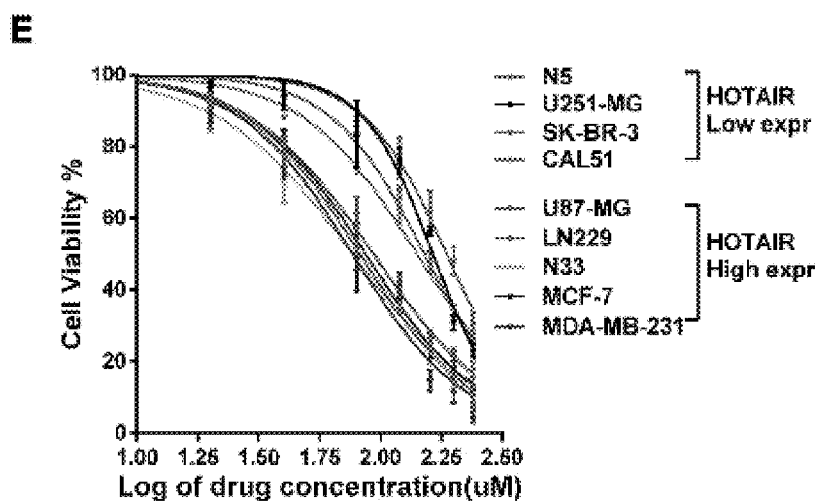
FIG. 1E: The toxicity test results of 36806 shown in cell counting kit-8 (CCK8) tests in multiple tumor cell lines.
Figure 2A:
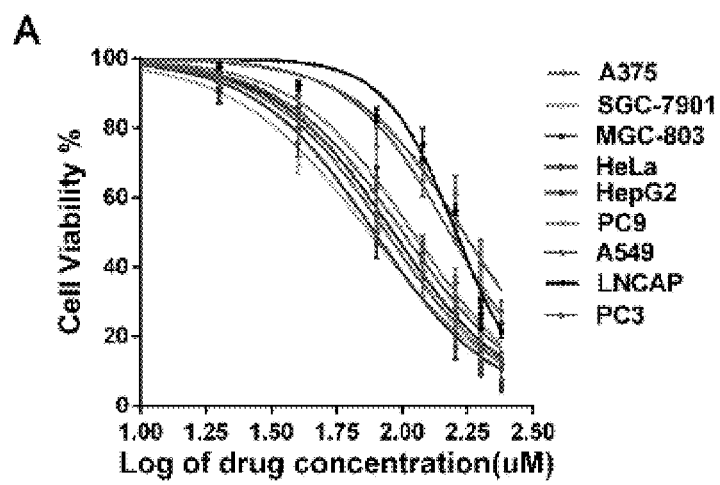
FIG. 2A: CCK8 test showed the dose-response curves of other cell lines.
Figure 2B:
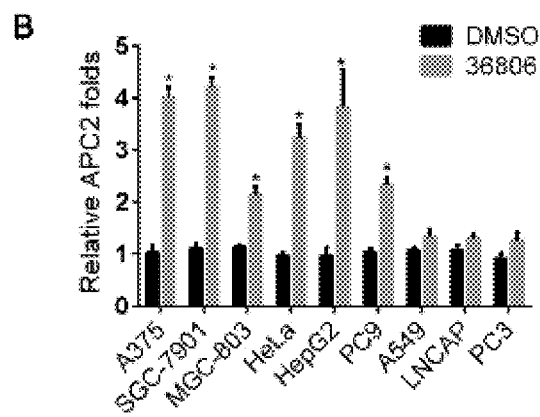
FIG. 2B: The variations in RNA level of a target gene 48 h after treating with 40 nM of 36806 in multiple tumor cell lines.
Figure 2C:
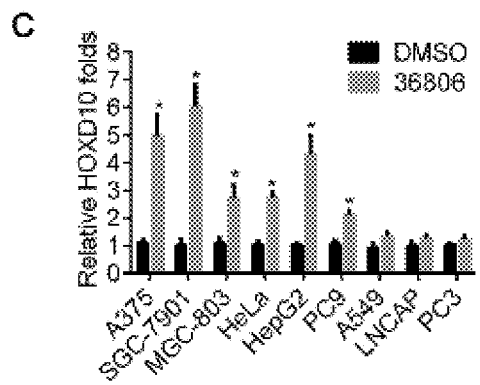
FIG. 2C: The variations in RNA level of a target gene 48 h after treating with 40 nM of 36806 in multiple tumor cell lines.
Figure 2D:
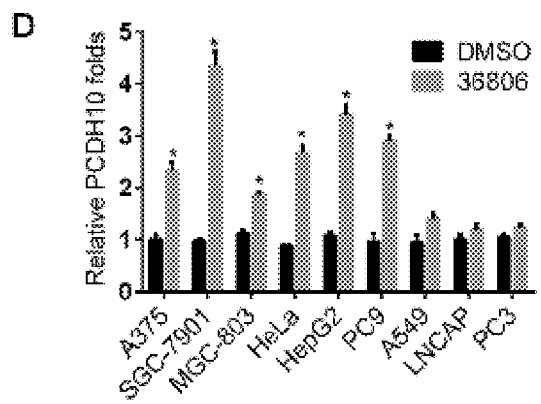
FIG. 2D: The variations in RNA level of a target gene 48 h after treating with 40 nM of 36806 in multiple tumor cell lines.
Figure 2E:
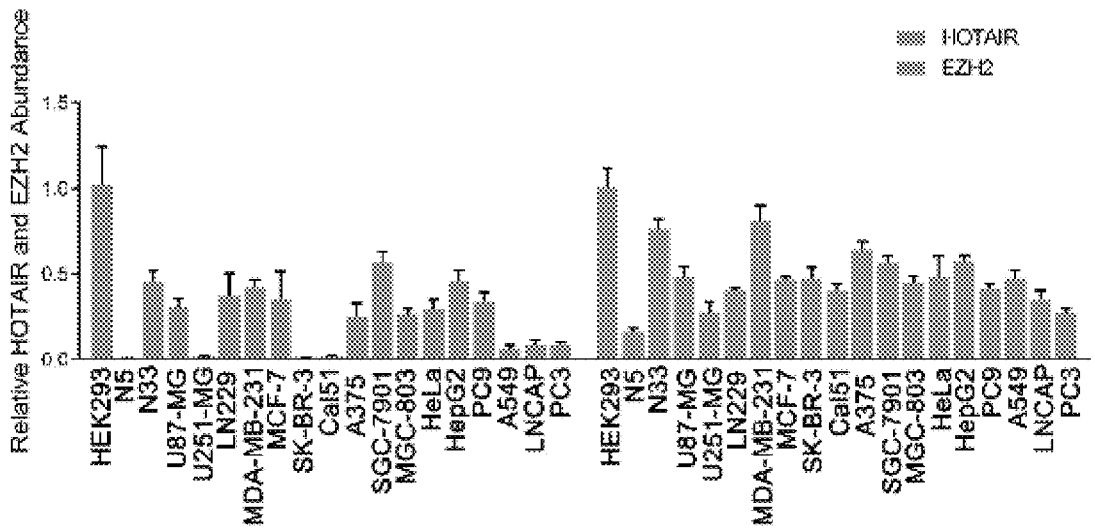
FIG. 2E: The background transcription levels of HOTAIR and EZH2 in multiple tumor cell lines detected by quantitative qPCR, in which HEK293 cells served as a standardized reference.
Figure 2F:
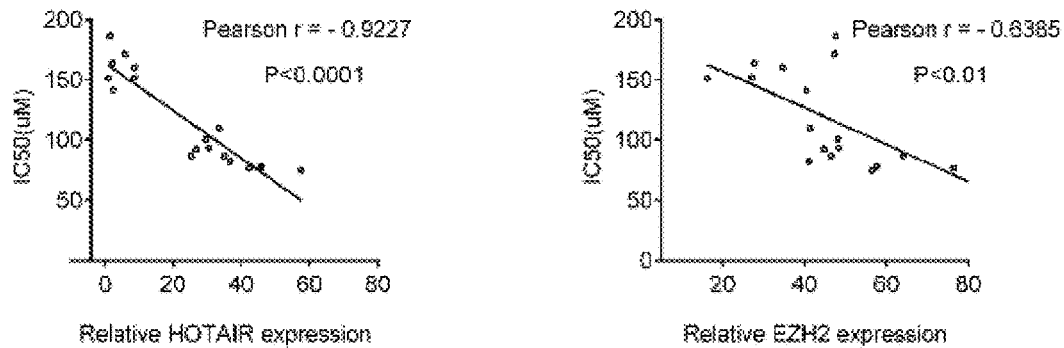
FIG. 2F: The correlation between the background HOTAIR and EZH2 levels of the tumor cell lines and corresponding IC50 was analyzed, and it was found that both HOTAIR and EZH2 were negatively correlated with IC50 and had a statistical significance.

Compound 36806 has a simple structure, small molecular weight, and is easy to synthesize. For example, compound 36806 may be synthesized by the route diagram shown in FIG. 1B. According to structural simulation, as shown in FIG. 1C, compound 36806 is capable of binding to a position between HOTAIR and EZH2, and can change the distribution of the surrounding electron cloud through π-π conjugation, to generate electronic mutual repulsion force with HOTAIR 5' domain and EZH2 protein domain, thereby interfering with the binding of HOTAIR 5' domain to EZH2. In the TCGA Pan-Cancer (https://xenabrowser.net/hub/) database, the expression levels of HOTAIR and EZH2 in 33 tumors were compared. As shown in FIG. 1D, it is found that in glioblastoma, breast cancer, cervical cancer, gastric cancer, melanoma, lung cancer and liver cancer, the expression levels of HOTAIR and EZH2 are relatively high, which means that HOTAIR and EZH2 may be sensitive to 36806. Toxicity tests were then performed in multiple tumor cell lines. As shown in FIG. 1E and FIG. 2A, it is found that the IC50 of 36806 was low in glioblastoma cell lines (U87-MG, LN229 and primary N33), breast cancer cell lines (MDA-MB-231 and MCF-7), cervical cancer HeLa cell lines, melanoma A375 cell lines, gastric cancer cell lines (SGC-7901 and MGC-803), liver cancer HepG2 cell lines and lung cancer PC9 cell lines. As shown in FIGS. 2B-2D, 36806 can up-regulate the expression level of HOTAIR target genes in all of the above cell lines. Therefore, 36806 has therapeutic effects on multiple tumors, including glioma, breast cancer, cervical cancer, gastric cancer, melanoma, lung cancer, and liver cancer. As shown in FIG. 2E, the relative background transcription levels of HOTAIR and EZH2 in multiple tumor cell lines were tested. As shown in FIG. 2F, the correlation between the IC50 of the cell lines and their HOTAIR levels and EZH2 levels were analyzed, and a statistically significant negative correlation was found. Therefore, 36806 is sensitive to tumor cell lines with high expression of HOTAIR and EZH2.

Figure 3A:
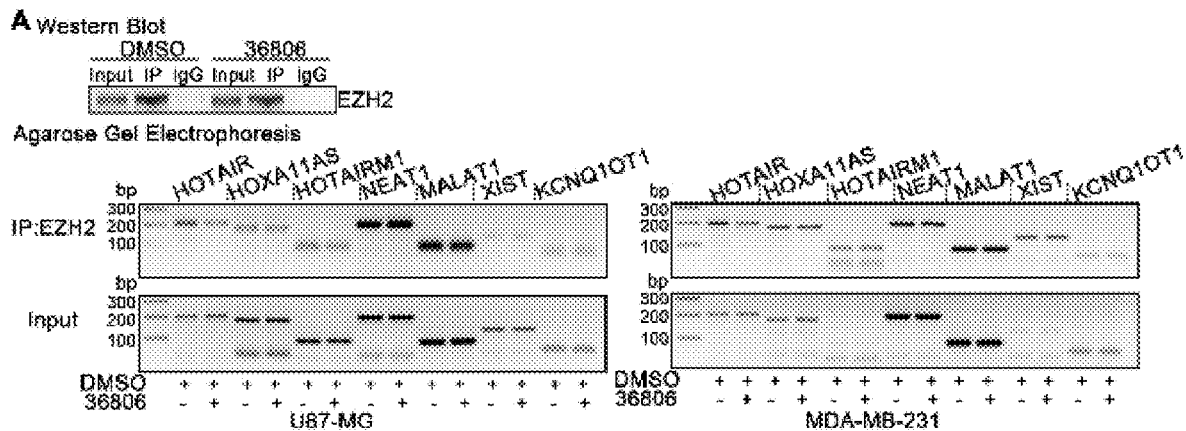
FIG. 3A: RIP experiments revealed that, at a concentration of 40 uM, 36806 only hindered the binding of HOTAIR to EZH2, but had no effect on the other six LncRNAs that had been proven to bind to EZH2.
Figure 3B:
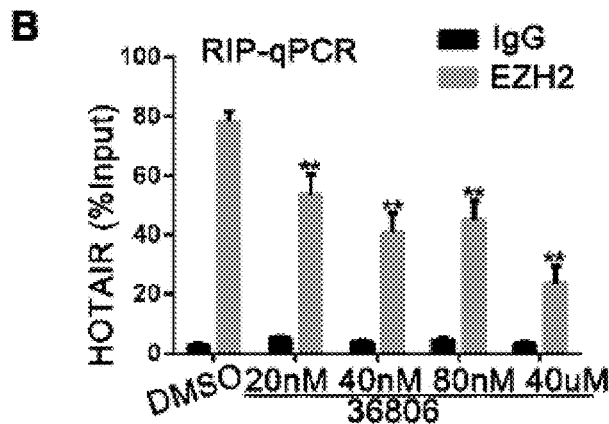
FIG. 3B: RIP results at a concentration gradient from 20 nM to 40 uM showed that the inhibition of 36806 on HOTAIR-EZH2 increased as the concentration increases.
Figure 3C:
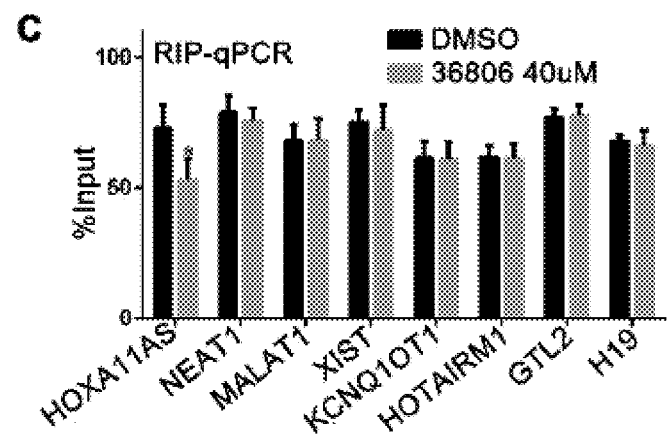
FIG. 3C: At a low concentration of 40 nM, 36806 had no significant effect on the binding of other lncRNAs to EZH2.
Figure 3D:
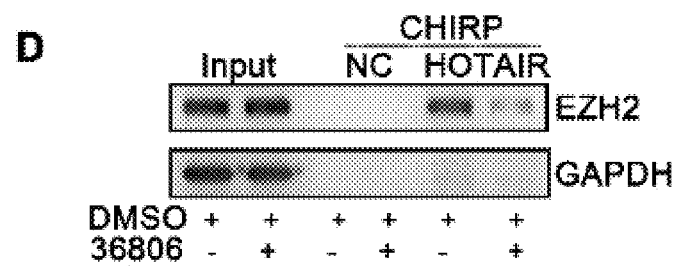
FIG. 3D: ChromatinIsolation by RNA purification (CHIRP) experiments further proved that 36806 can effectively hinder the binding of HOTAIR to EZH2.
Figure 3E:
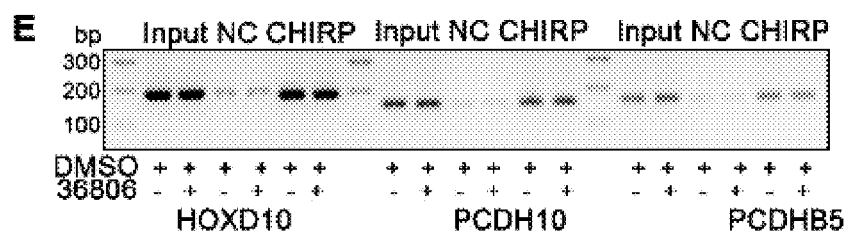
FIG. 3E: CHIRP experiments further proved that 36806 did not affect the binding of HOTAIR to target genes.
Figure 3F:
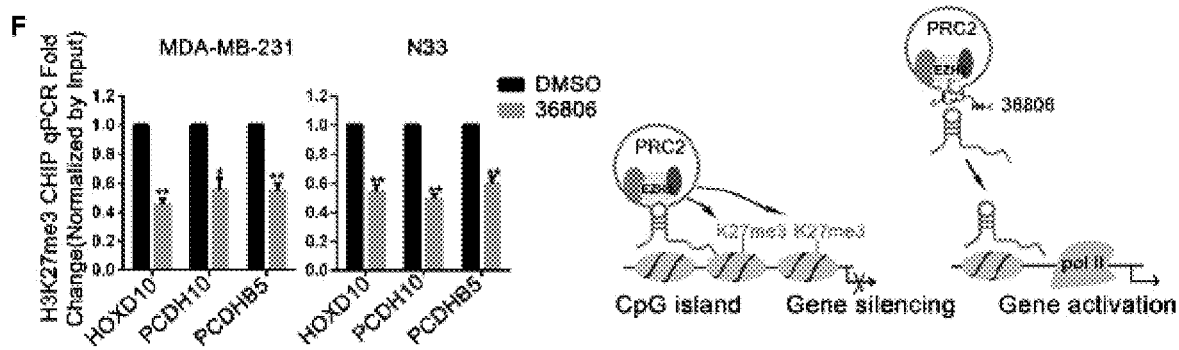
FIG. 3F: Chromatin immunoprecipitation (CHIP) experiments verified that 36806 affected the recruitment of PRC2 by HOTAIR after hindering the binding of HOTAIR to EZH2, such that the level of H3K27me3 in the promoter region of the target genes was reduced and the target genes were transcriptionally activated.

Embodiment 2 36806 can Specifically Interfere with the Binding of HOTAIR to EZH2, Affect the Recruitment of PRC2 by HOTAIR, Reduce the Level of H3K27Me3 at the Target Gene Sites, and Enable the Transcriptional Expression of the Target Genes As shown in FIG. 3A, RIP experiments revealed that, at a concentration of 40 uM, 36806 only hindered the binding of HOTAIR to EZH2, but had no effect on the other six LncRNAs that had been proven to bind to EZH2. As shown in FIG. 3B, RIP results at a concentration gradient from 20 nM to 40 uM showed that the inhibition of 36806 on HOTAIR-EZH2 increased as the concentration increases. As shown in FIG. 3C, at a low concentration of 40 nM, 36806 had no significant effect on the binding of other lncRNAs to EZH2. Therefore, the inhibiting effect of 36806 on HOTAIR-EZH2 is specific. As shown in FIGS. 3D and 3E, the CHIRP experiments further proved that 36806 with a concentration of 40 nM can effectively hinder the binding of HOTAIR-EZH2 and interfere with the recruitment of PRC2 by HOTAIR without affecting the binding of HOTAIR to the target genes. Finally, as shown in FIG. 3F, the CHIP experiments verified that 36806 affected the recruitment of PRC2 by HOTAIR after hindering the binding of HOTAIR-EZH2, such that the level of H3K27me3 in the promoter region of the target genes was reduced and the target genes were transcriptionally activated.

Figure 4A:
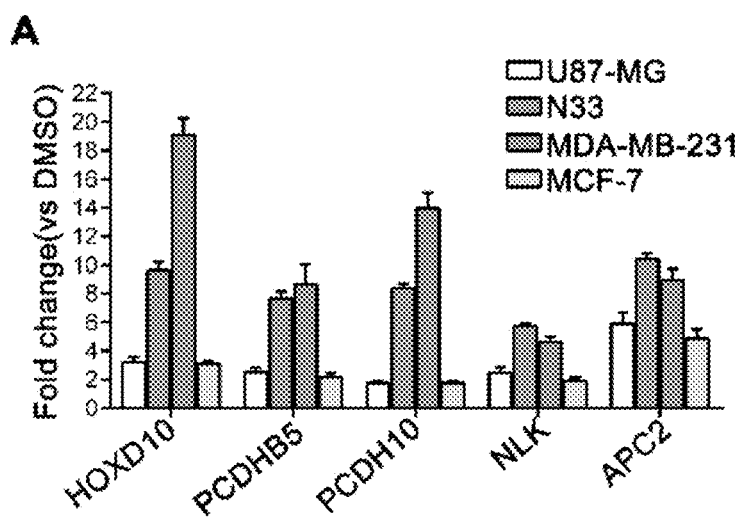
FIG. 4A: RNA levels change of target genes in glioma and breast cancer cell lines after treating with 40 uM of 36806 for 48 hours.
Figure 4B:
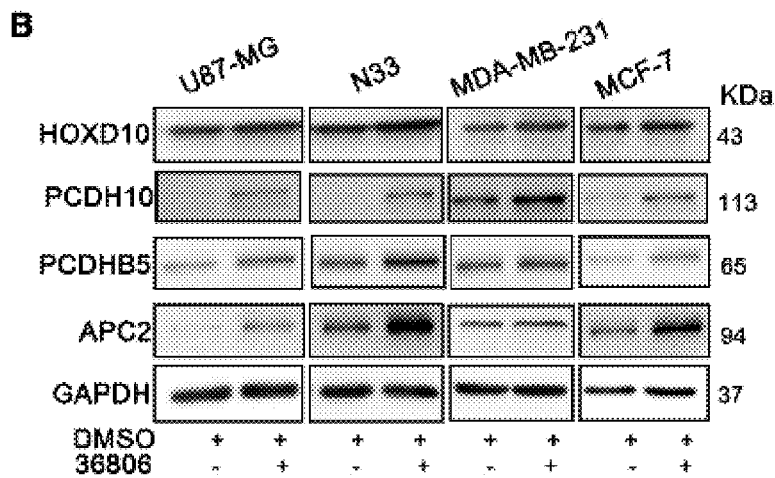
FIG. 4B: Western blot assay proved that the protein level of the target genes changed after treating with 40 uM of 36806 for 48 hours.

Embodiment 3 36806 can Increase the Transcription and Expression Levels of HOTAIR Target Genes at Very Low Concentrations As shown in FIGS. 4A and 4B, in glioma and breast cancer cell lines, a high concentration of 36806 (40 uM) can increase the mRNA level and protein level of HOTAIR's target genes HOXD10, PCDH10, PCDHB5, NLK, and APC2. As shown in FIGS. 4C and 4D, at a low concentration gradient of 10 nM to 10 uM, both RNA level and protein level of the above target genes were increased, and the increase in the RNA level of each target gene did not show a concentration-dependent characteristic, but had an optimal concentration. Therefore, 36806 is capable of inhibiting the binding of HOTAIR to EZH2 at low concentrations and interfering with the recruitment of PRC2 to target genes, to relieve the target genes from silent suppression of histone methylation, thereby altering the function of epigenetic regulation.

Embodiment 4 36806 Inhibits the WNT Signal Path, Reverses Tumor EMT, and Reduces Tumor Invasion and Metastasis by Transforming the Level of an HOTAIR Target Gene APC2

Figure 5A:
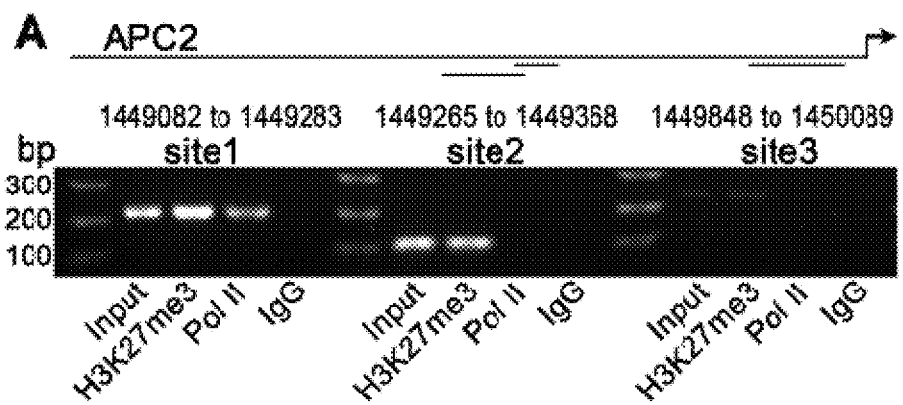
FIG. 5A: The Site1 region before the transcription initiation of APC2 is a transcription promoter region of APC2 and a binding region of H3K27me3.
Figure 5B:
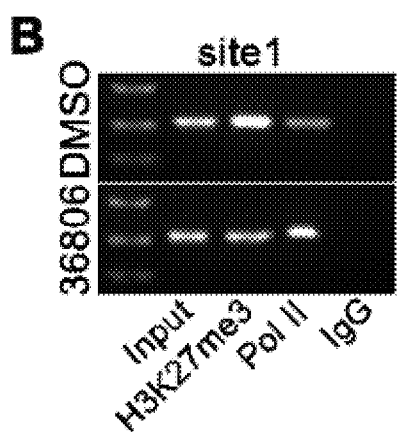
FIG. 5B: After the treatment with 36806, the binding of H3K27me3 in Site1 region was weakened, and the binding of RNA polymerase II was strengthened.
Figure 5C:
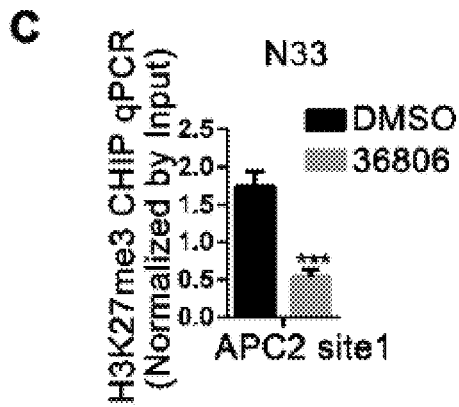
FIG. 5C: CHIP qPCR proved that after 36806 treatment, the binding of H3K27me3 in the promoter region of the target genes was weakened.
Figure 5D:
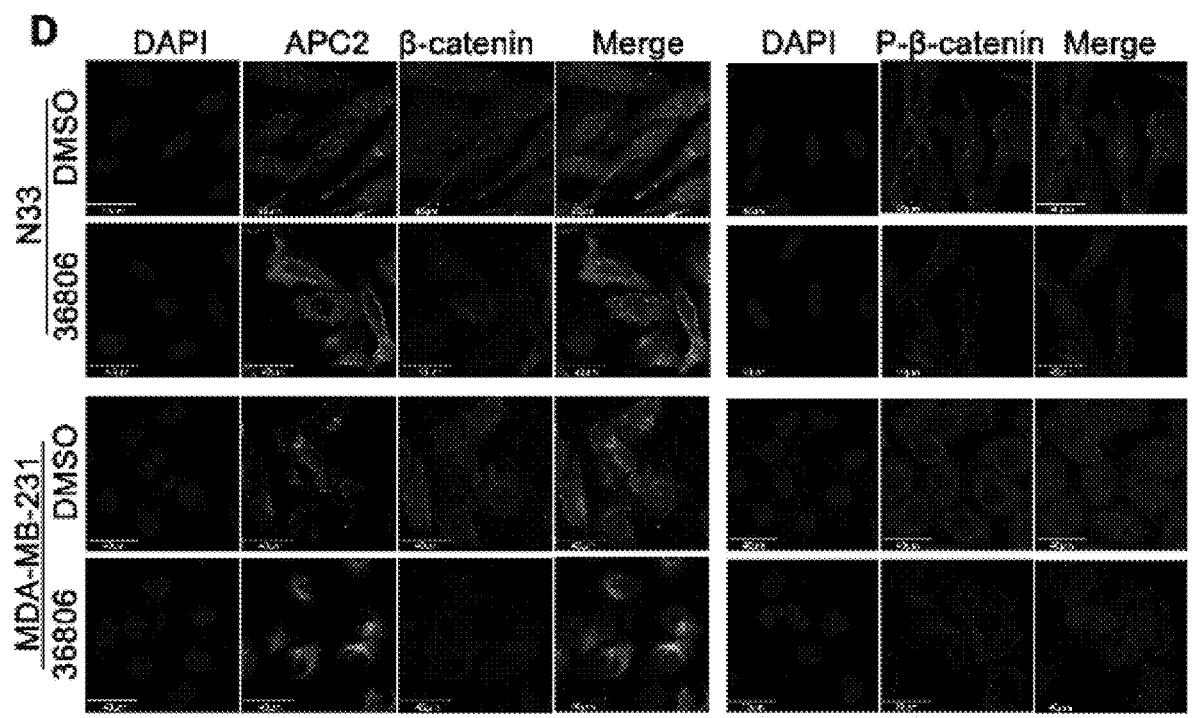
FIG. 5D: The immunofluorescence test proved that the expression of the target gene APC2 increased, while the distribution of beta-catenin and p-beta-catenin in nucleus and cytoplasm decreased.
Figure 5E:
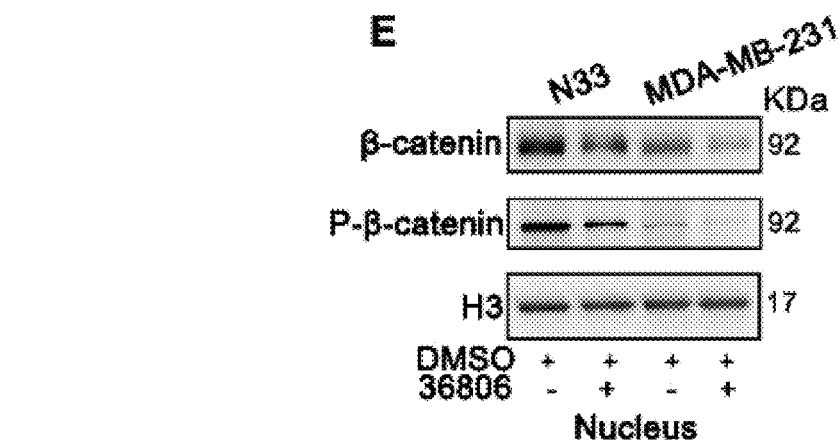
FIG. 5E: Western Blot (WB) experiments of nuclear extracts proved that the levels of beta-catenin and p-beta-catenin decreased.
Figure 5F:
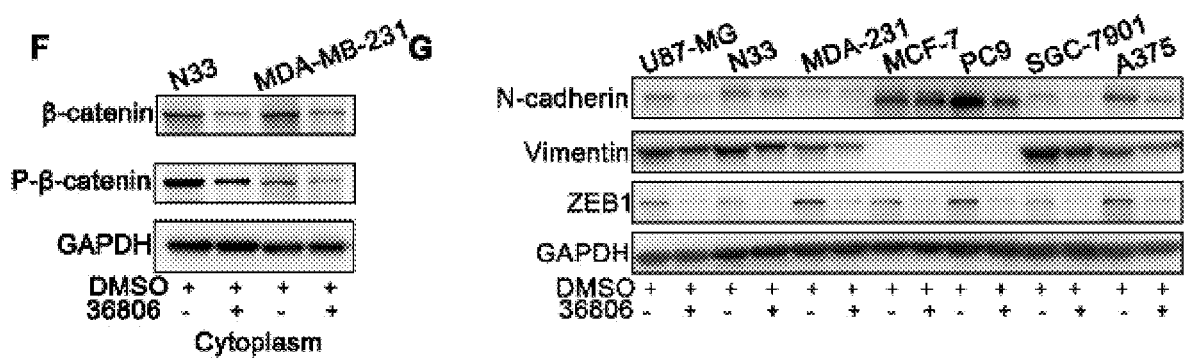
FIG. 5F: WB experiments proved that the levels of beta-catenin and p-beta-catenin in the cytoplasm decreased, and the expression of downstream EMT-related genes of beta-catenin decreased.
Figure 5G:
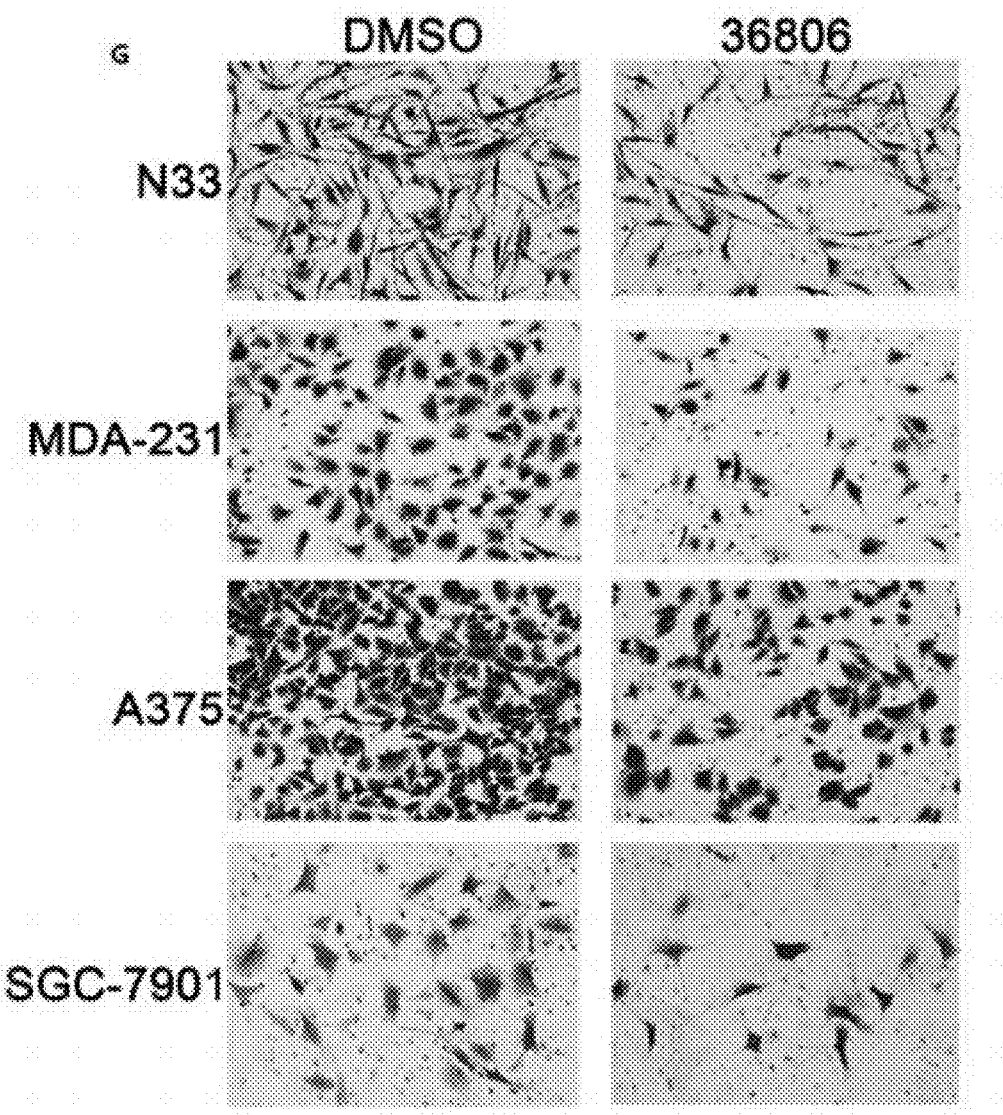
FIG. 5G: Transwell assay shows inhibition of cell invasion by 36806 in indicated cancer cell lines.
Figure 5H:
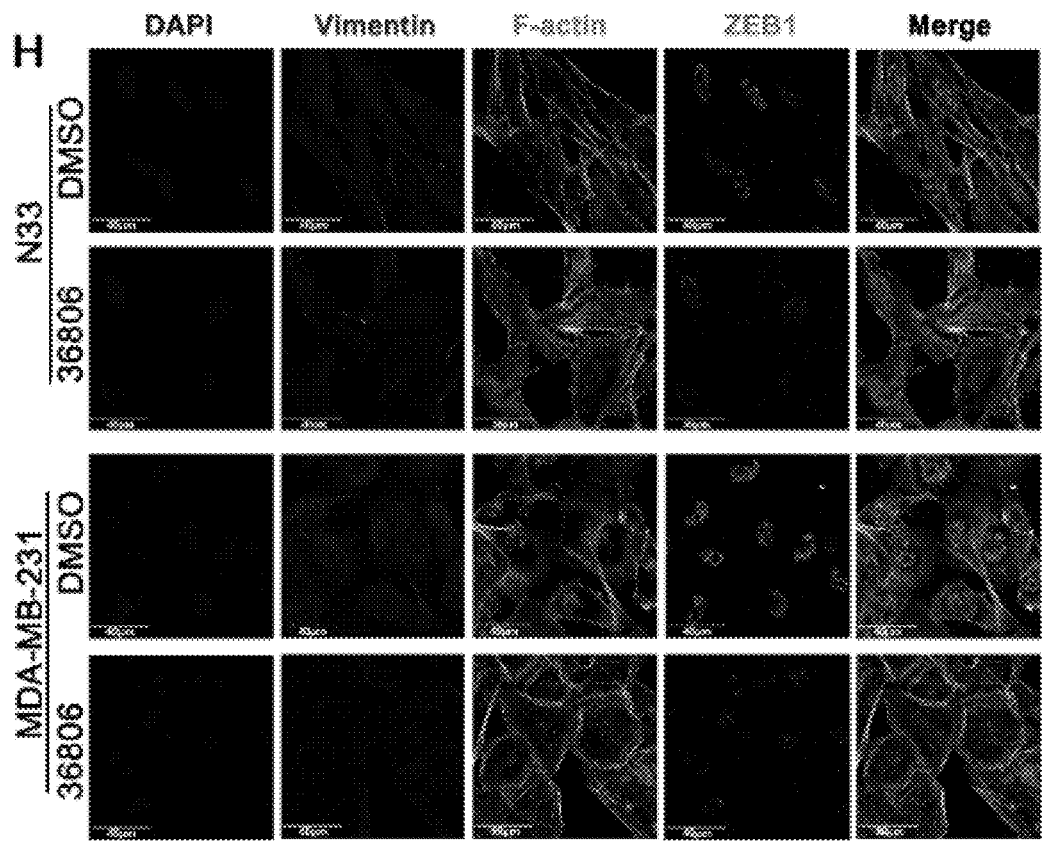
FIG. 5H: Transwell experiments proved that low-dose 40 nM of 36806 can reduce the invasion of glioblastoma, breast cancer, melanoma and gastric cancer cell lines.

Among the three predicted H3K27me3 binding sites in the promoter region of the target gene adenomatous polyposis *coli* 2 (APC2), site1 is a significant binding region of H3K27me3 (FIG. 5A). After the treatment with 36806, the binding of H3K27me3 in site1 region was weakened, and the binding of RNA polymerase II was strengthened (FIGS. 5B and 5C). It shows that 36806 reduces the methylation of the lysine at position 27 of histone H3 in the promoter region of the target gene APC2 by inhibiting the binding of HOTAIR to EZH2 and reducing the recruitment of PRC2 by HOTAIR, such that more RNA polymerase II binds to the HOTAIR to promote transcription and expression. APC2 is a tumor suppressor gene that can participate in the degradation of beta-catenin by ubiquitination and can inhibit the WNT signal path. The increased expression of APC2 can boost the degradation of beta-catenin. The nucleus-cytoplasm distribution of beta-catenin of cells in the treated group was decreased compared with that of the DMSO group (FIGS. 5D-5F). In this way, the downstream transcription of beta-catenin is inhibited, the expression of downstream EMT-related gene of multiple tumor cell lines is inhibited, and the protein expression is reduced (FIGS. 5G). Therefore, the invasion of tumor cells is weakened (FIG. 5H). Therefore, 36806 can inhibits the WNT signal path, reverses tumor EMT, and reduces tumor invasion and metastasis by increasing the expression level of target gene APC2.

Figure 6A:
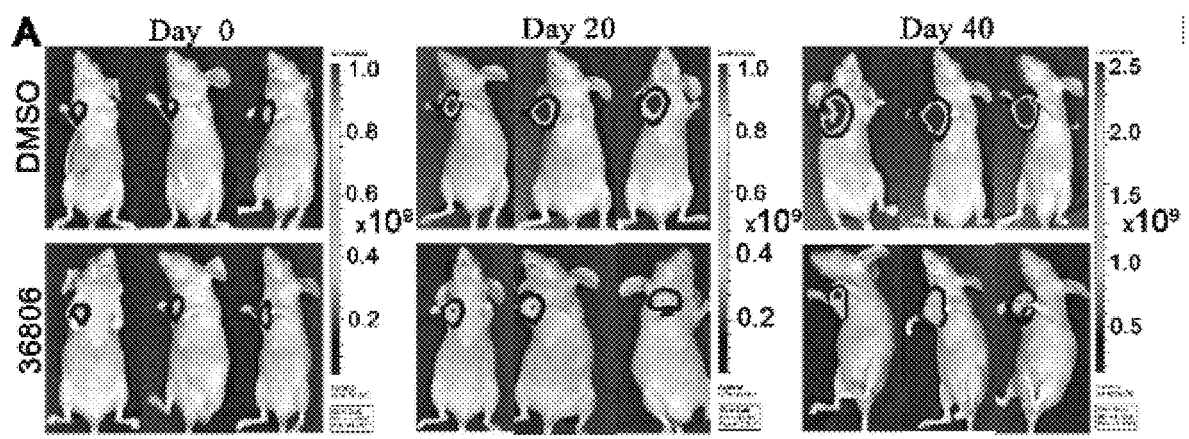
FIG. 6A: Bioluminescence imaging showed that 36806 can significantly inhibit the growth of a mouse breast cancer orthotopic model.
Figure 6B:
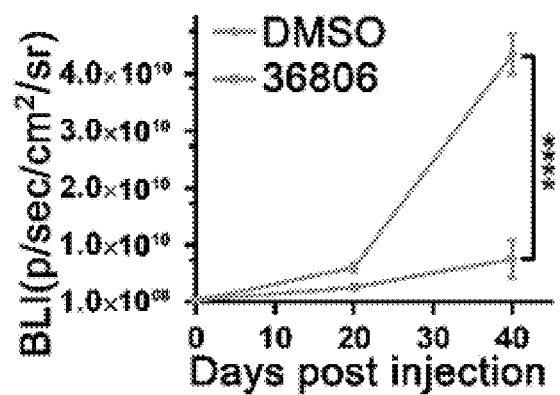
FIG. 6B: Quantitative and statistical analysis of the bioluminescence results showed that 36806 significantly inhibited tumor growth.
Figure 6C:
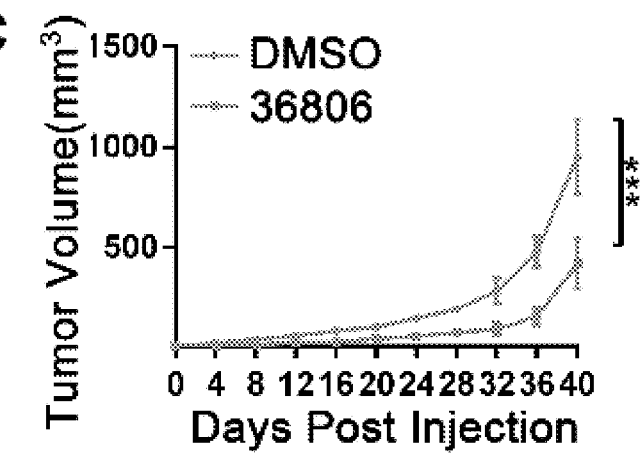
FIG. 6C: The body surface volume measurement results showed that the tumor volume of mice in the 36806 group was significantly smaller than that of the DMSO group.
Figure 6D:
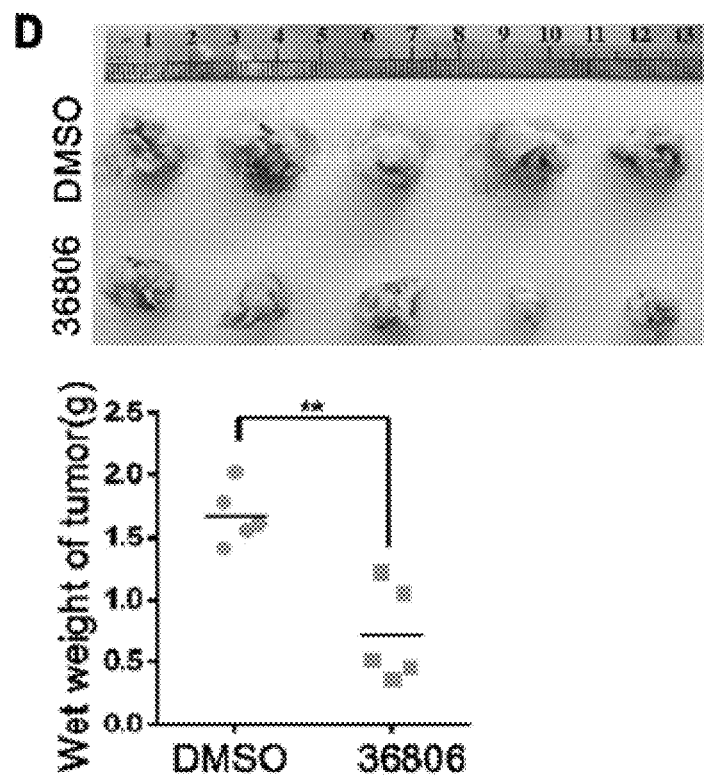
FIG. 6D: After surgical dissection of the tumor in situ, it was found that the size and wet weight of the tumor in the 36806 group were lower than those in the DMSO group.
Figure 6E:
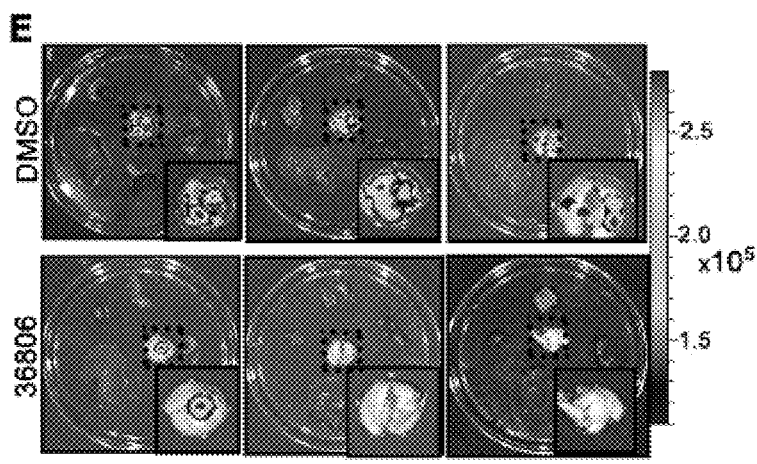
FIG. 6E: Bioimaging results of heart, liver, spleen, lung and kidney in mice showed that 36806 significantly inhibited the orthotopic lung metastasis of breast cancer.
Figure 6F:
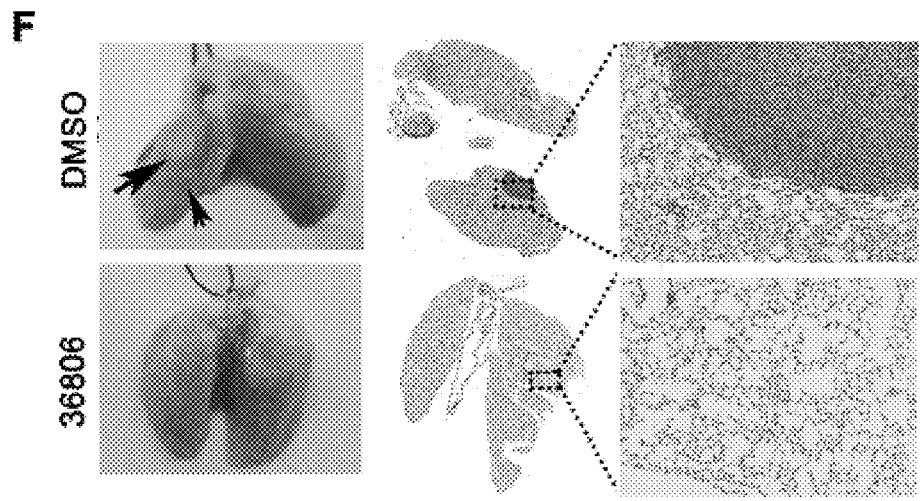
FIG. 6F: Photos of the lung of the mouse and the hematoxylin-eosin (HE) staining result clearly showed that the lung of the mouse in the DMSO group had multiple metastases (black arrows), while the mouse in 36806 group had no tumor metastasis.
Figure 6G:
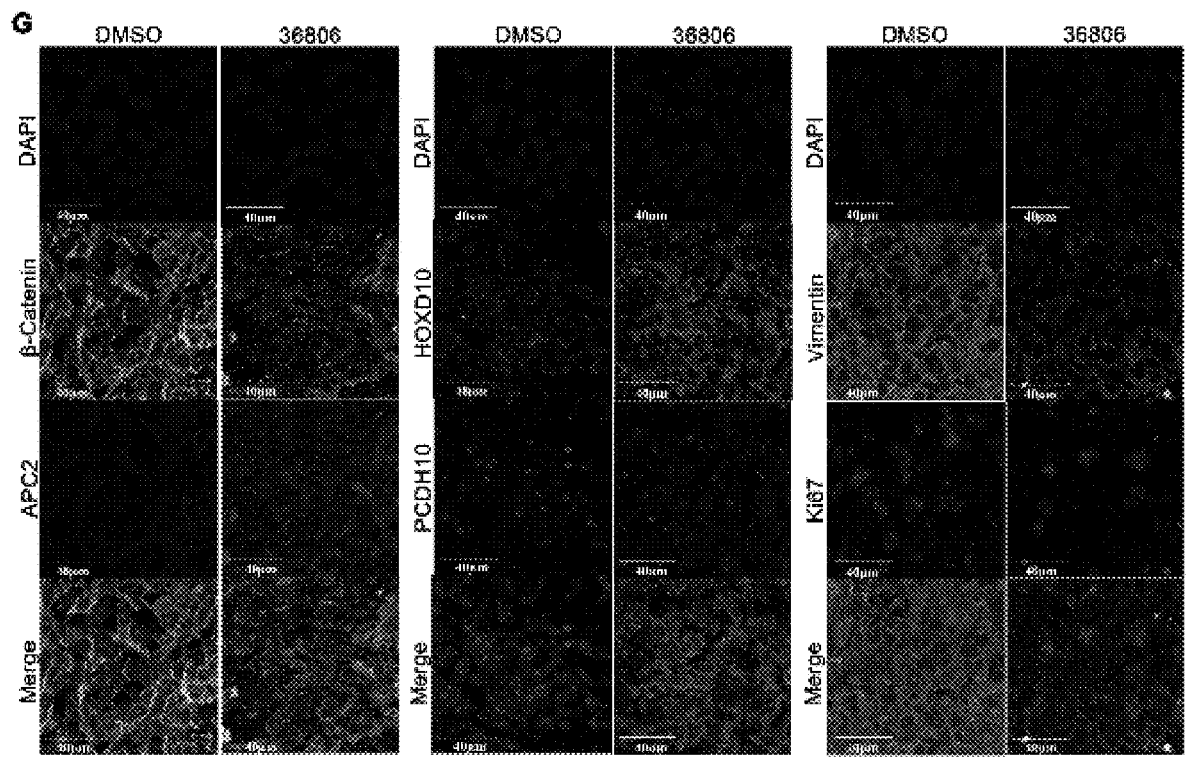
FIG. 6G: Immunofluorescence in paraffin sections of mouse tissues showed that the expressions of target genes APC2, PCDH10 and HOXD10 were increased, and the expressions of beta-catenin, Ki67 and Vimentin were decreased.

Embodiment 5 36806 can Inhibit the Proliferation and Metastasis of Breast Cancer Orthotopic Model To further verify the anti-tumor effect of 36806 in vivo, a breast cancer orthotopic model is established by using a MDA-MB-231 cell line. After intraperitoneal injection at a dose of 50 mg/kg for 20 days and 40 days, the tumor size of mice in the treated group was significantly reduced compared with that of the DMSO group (FIGS. 6A-6B). The tumor volume measured on the body surface was reduced, and the size and wet weight of the tumor after dissection were reduced as well (FIGS. 6C-6D). Imaging of the heart, liver, spleen, lung and kidney showed that the probability and scope of lung metastasis in mice in the treated group is smaller (FIG. 6E). HE staining confirmed the orthotopic lung metastasis of breast cancer (FIG. 6F). Immunofluorescence of tissue sections showed that after 36806 treatment, the expression of APC2 was increased and the expression of beta-catenin was decreased; the expression of target genes HOXD10 and PCDH10 was increased; the expression of proliferation index Ki-67 and EMT index Vimentin was decreased (FIG. 6G). The above is consistent with the results of in-vitro experiments, that is, 36806 can inhibit the proliferation and metastasis of breast cancer orthotopic model.

Embodiment 6 36806 can Enhance the Pharmacodynamic Effect of the EZH2 Inhibitor DZNEP and Reduce the Dosage of the DZNEP Anti-Tumor Drug 36806 can specifically hinder the binding of HOTAIR to EZH2, reshape the epigenetic regulation mediated by HOTAIR, and work at a very low drug concentration, therefore, it is envisaged that 36806 may be used in combination with an epigenetic therapy drug EZH2 inhibitor DZNEP. The English name of DZNEP is 3-Deazaneplanocin A. The molecular formula for DZNEP is C12H14N4O3. The molecular weight of DZNEP is 262.269 g/mol. The structural formula of DZNEP is

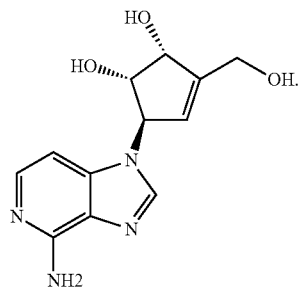 [SMILES: Nc1nccc2c1ncn2[C@@H]1C=C(CO)[C@@H](O)[C@H]1O]

The CAS number of DZNEP is 120964-45-6.

Figure 7A:
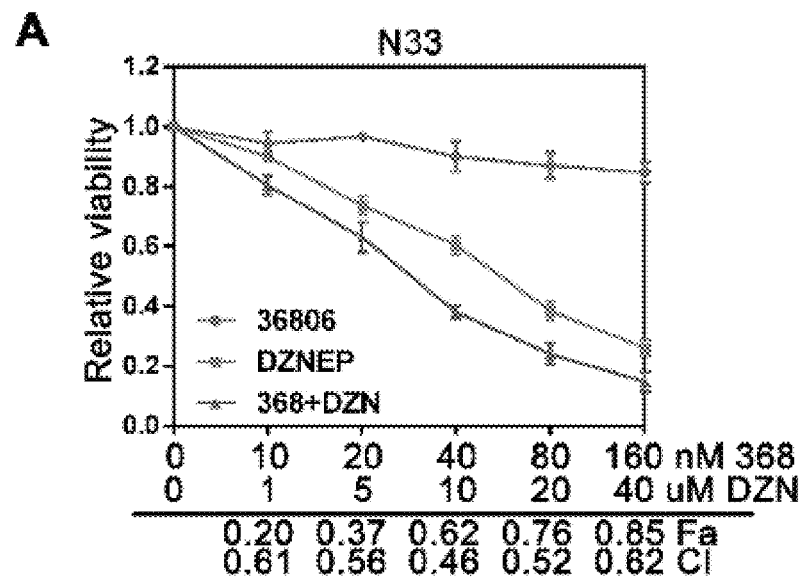
FIG. 7A: Dose-response curves of 36806, DZNEP and 36806 in combination with DZNEP in N33 cell viability experiments. The combination index (CI) calculated by CalcuSyn software revealed that 36806 could enhance the effect of DZNEP.
Figure 7B:
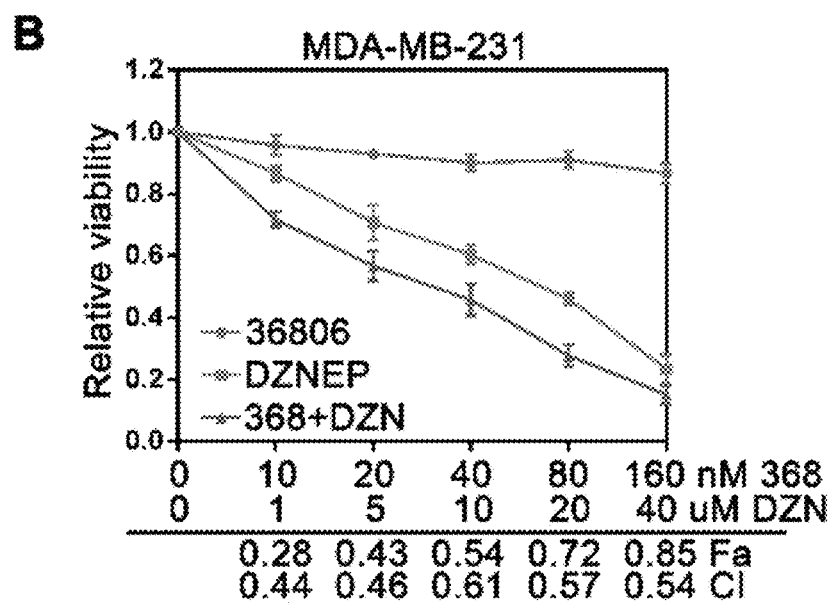
FIG. 7B: Dose-response curves of 36806, DZNEP and 36806 in combination with DZNEP in MDA-MB-231 cell viability experiments. The combination index (CI) calculated by CalcuSyn software revealed that 36806 could enhance the effect of DZNEP.
Figure 7C:
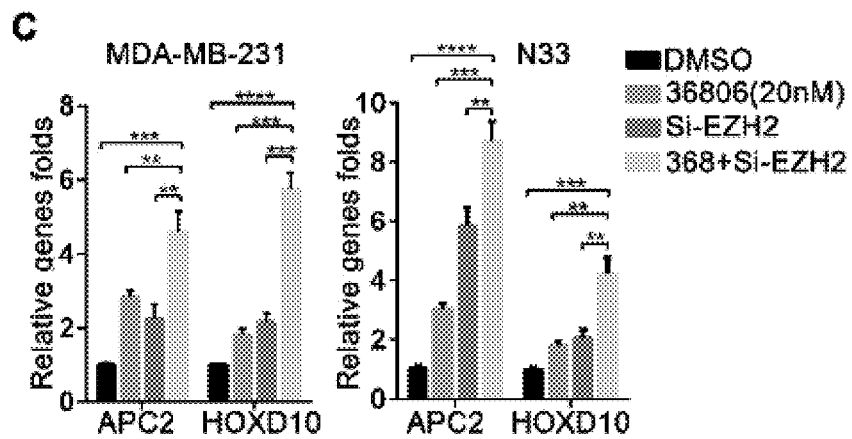
FIG. 7C: qPCR proved that 36806 in combination with the interfering RNA of EZH2 could further increase the RNA levels of HOTAIR's target genes APC2 and HOXD10.
Figure 7D:
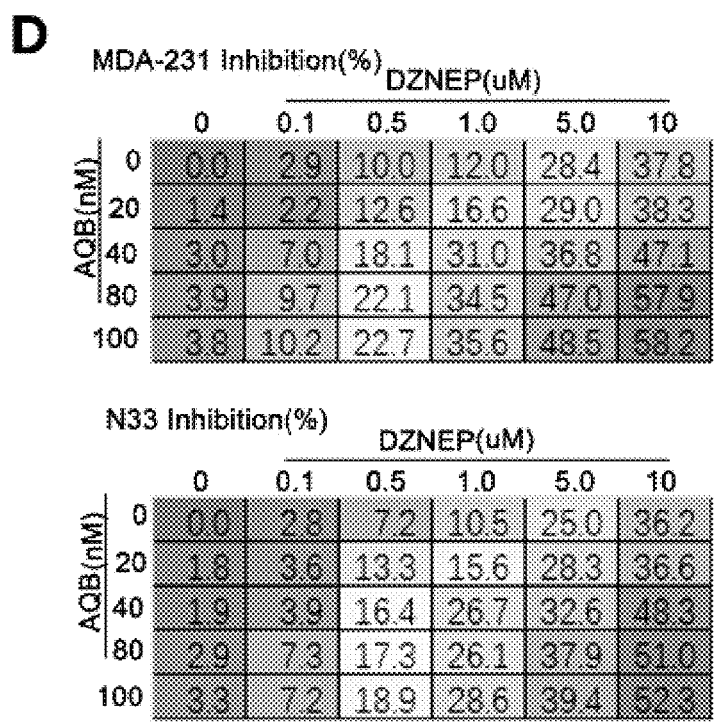
FIG. 7D: Cell inhibition rate of N33 and MDA-MB-231 cell lines under the treatment of 36806 in combination with DZNEP.
Figure 7E:
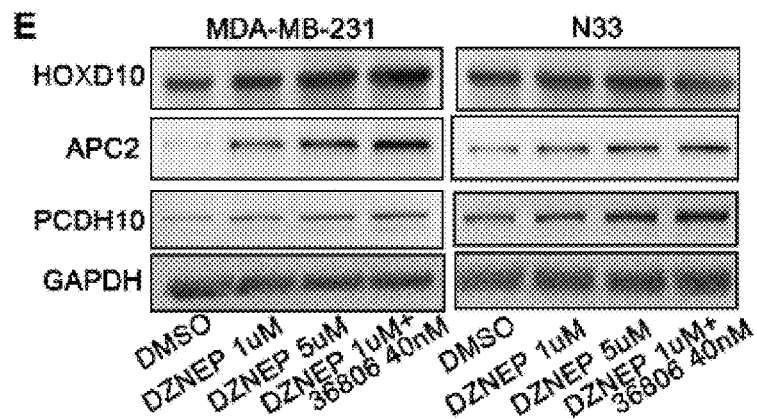
FIG. 7E: Western blot assays proved that 40 nM of 36806 in combination with 1 uM of DZNEP could increase the protein level of the target genes, and the effect was the same as or even better than that of 5 uM of DZNEP alone.
Figure 7F:
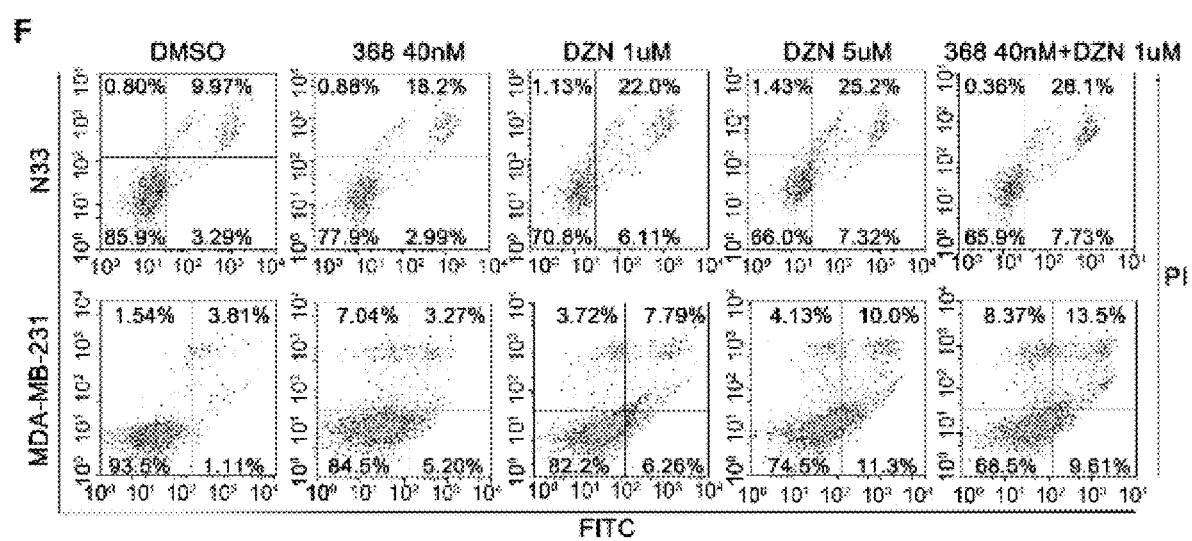
FIG. 7F: Flow cytometry apoptosis assay further proved that 36806 in combination with DZNEP could enhance the pro-apoptotic effect of DZNEP, such that the DZNEP with ⅕ dose had the same apoptotic effect as that of the DZNEP with full dose.

The combination index (CI) of 36806 and DZNEP was measured by CalcuSyn software. It was found that the CI values were less than 0.7, indicating that 36806 can enhance the tumor inhibiting effect of DZNEP (FIGS. 7A-7B). After the transfection of EZH2 interfering RNA, combined with 36806 treatment, the transcription level of HOTAIR's target genes was higher (FIG. 7C). The toxicity test further proved that a low dose of 36806 can enhance the effect of DZNEP, and suggested that 40 nM 36806 and 1 uM DZNEP is an appropriate combined concentration. When used in combination with low-dose 36806, the dosage of DZNEP can be reduced by ⅘ (FIG. 7D). Western results showed that the effect of 40 nM 36806 in combination with 1 uM DZNEP can reach or even exceed that of 5 uM DZNEP (FIG. 7E). The results of flow cytometry apoptosis assay further proved that 36806 can enhance the pro-apoptotic effect of DZNEP (FIG. 7F). The above results indicated that when used in combination with 36806, the dosage of DZNEP can be reduced by ⅘ while achieving anti-tumor effects.

Figure 8A:
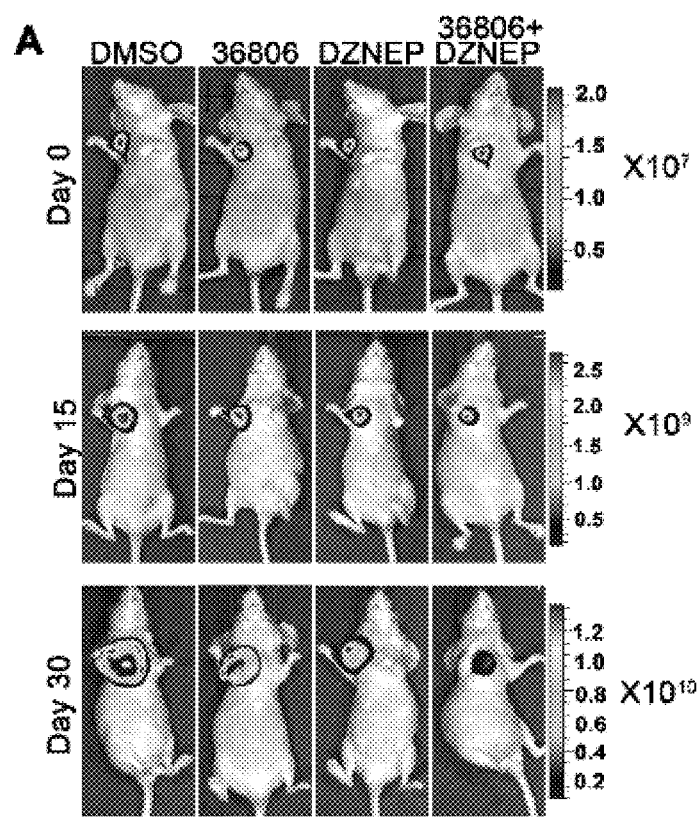
FIG. 8A: Bioluminescence images proved that 36806 in combination with DZNEP could significantly inhibit tumor growth.
Figure 8B:
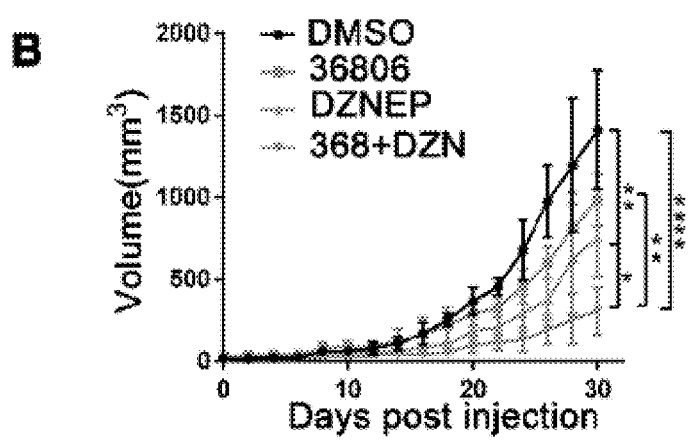
FIG. 8B: The tumor volume measured on the body surface in the combination group was the lowest and lower than that in the DZNEP full dose group.
Figure 8C:
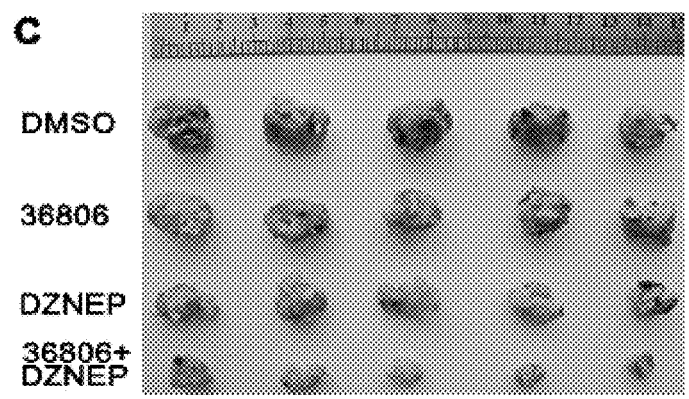
FIG. 8C: After tumor dissection, it was obvious that the tumor volume of the mice in the combination group was smaller.
Figure 8D:
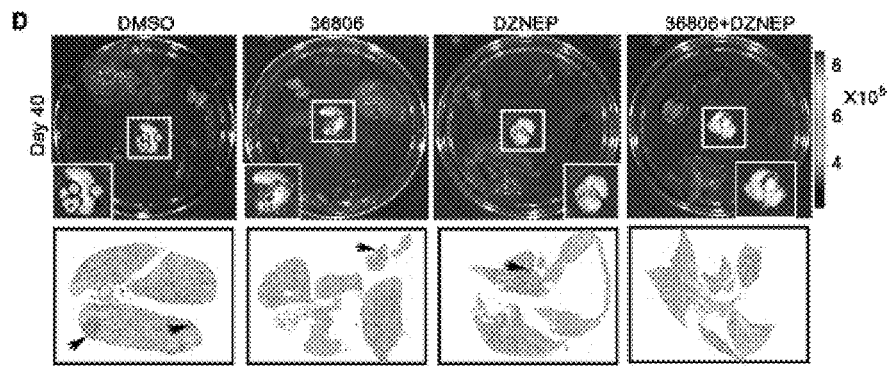
FIG. 8D: Bioluminescence images of the heart, liver, spleen, lung, and kidney showed that the combination drug therapy could effectively inhibit lung metastasis of breast cancer.
Figure 8E:
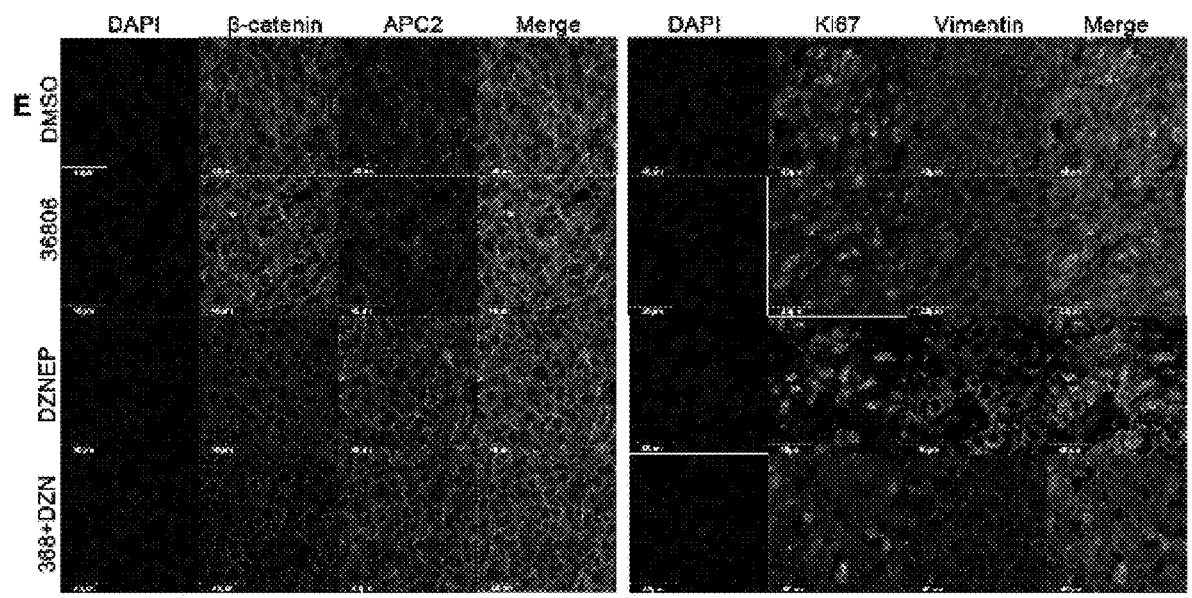
FIG. 8E: Immunofluorescence of mouse tissue sections showed that in the combination group, APC2 was significantly increased, while the expressions of beta-catenin, Ki67 and Vimentin were decreased.

Embodiment 7 Combination of Low-Dose 36806 with ⅕ Dose of DZNEP can Inhibit Proliferation and Metastasis of Breast Cancer Orthotopic Model A breast cancer orthotopic model is established by using a MDA-MB-231 cell line. 0.2 mg/kg 36806 in combination with 0.2 mg/kg DZNEP served as a combination group (the molar ratio was about 1:1), 0.2 mg/kg 36806 and 1 mg/kg DZNEP served as single-drug groups, and DMSO served as a control group. The results showed that the tumor imaging size, measured tumor volume, and dissected tumor size of the combination group were significantly reduced compared with those of other groups, and the lung metastasis was significantly reduced as well (FIGS. 8A-8C). The imaging results of the heart, liver, spleen, lung and kidney as well as HE staining showed that the combination group was more effective in inhibiting the lung metastasis of tumors (FIG. 8D). Fluorescence of tissue sections showed that the expression of target gene APC2 was increased, the expression of beta-catenin was decreased, and the expression of Ki-67 and Vimentin was decreased (FIG. 8E).

Figure 9A:
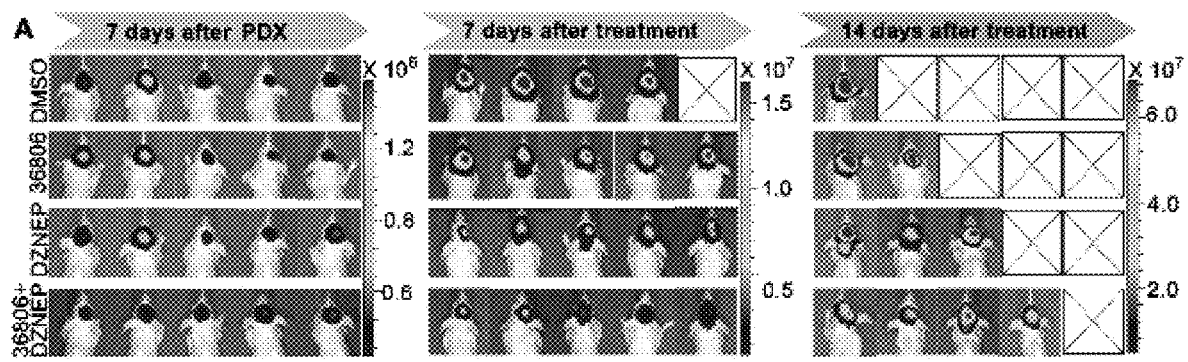
FIG. 9A: Bioluminescence showed that the tumor volume of mice in the combination group was smaller.
Figure 9B:
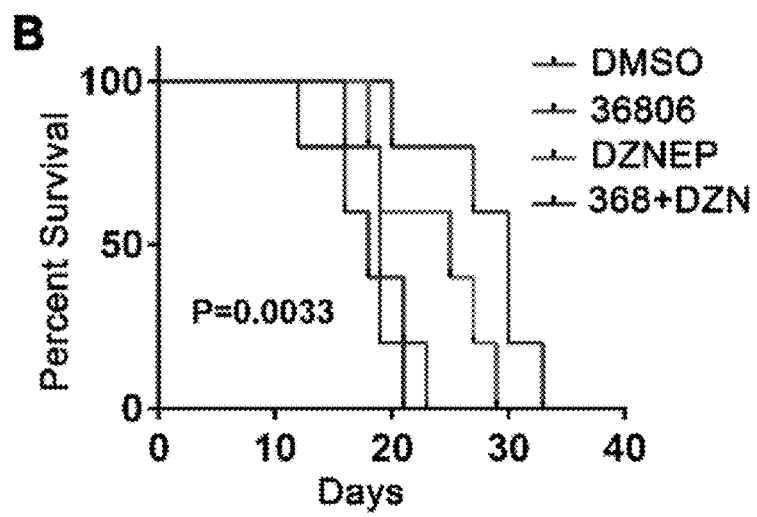
FIG. 9B: Survival analysis suggested that the mice in the combination group had a longer life span.
Figure 9C:
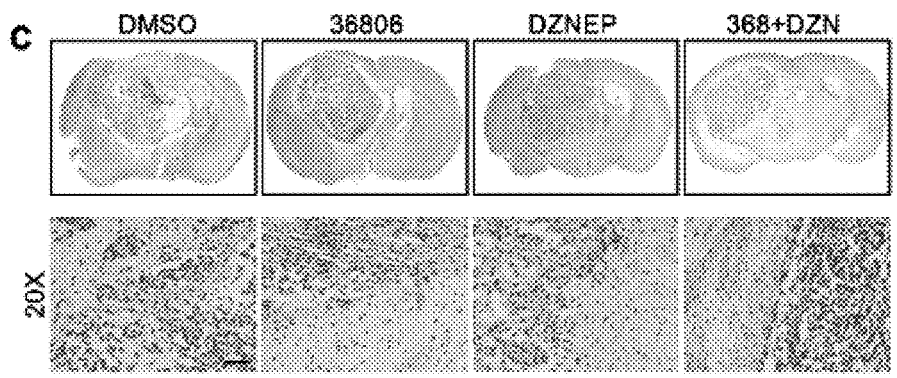
FIG. 9C: Mouse brain sections showed that the tumor volume in the combination group was smaller, and the HE staining showed that the tumor boundary was smoother.
Figure 9D:
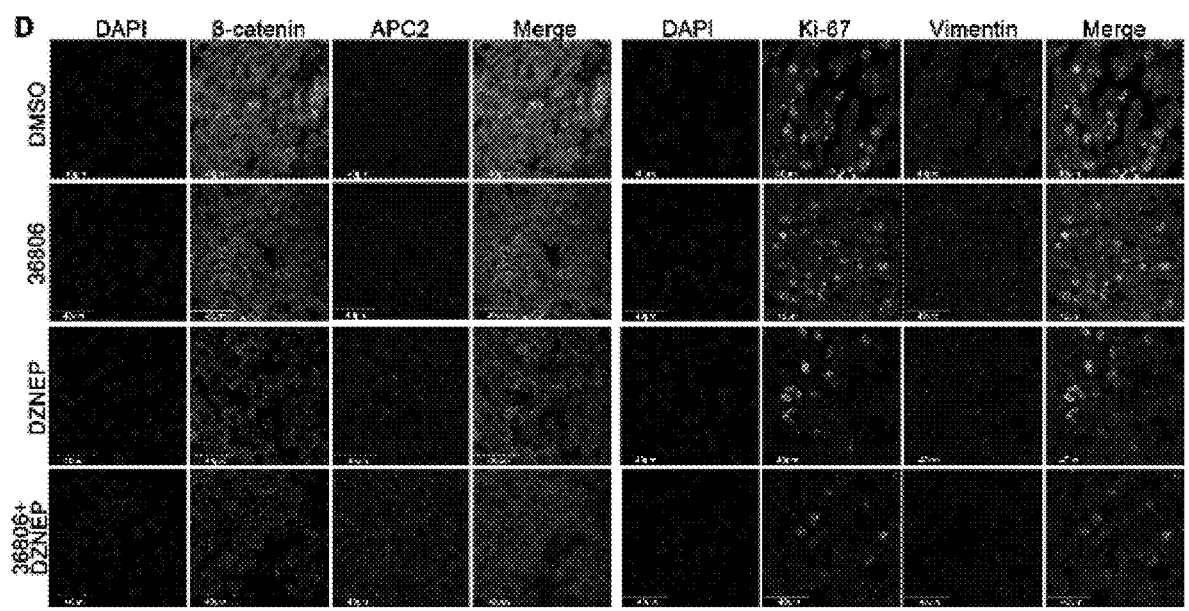
FIG. 9D: Immunofluorescence of mouse brain sections showed that in the combination group, the expression of APC2 was significantly increased, while the expressions of beta-catenin, Ki67 and Vimentin were decreased.

Embodiment 8 Combination of Low-Dose 36806 with ⅕ Dose of DZNEP can Inhibit Proliferation and Metastasis of Glioma PDX Model The results of the glioblastoma PDX model showed that the mice in the combination group had smaller tumor sizes (FIG. 9A) and longer life spans (FIG. 9B). The effect of combination group was even better than that of the full-dose DZNEP. HE staining showed that not only the size of the tumor in the combination group was smaller, but the boundary was smoother and clearer, indicating that the combination drug therapy can reduce tumor invasion and metastasis (FIG. 9C). Fluorescence of tissue sections showed that the expression of target gene APC2 was increased, the expression of beta-catenin was decreased, and the expression of Ki-67 and Vimentin was decreased (FIG. 9D).

The above embodiments are intended to illustrate the disclosed embodiments of the present disclosure and are not understood as restrictions on the present disclosure. In addition, various modifications of the present disclosure, as well as variations of the methods and compositions of the disclosure, will be apparent to those skilled in the art without departing from the scope of the present disclosure. While the disclosure has been described in detail in connection with various specific preferred embodiments thereof, however, it should be understood that the present disclosure should not be limited to these specific embodiments. In fact, various modifications to the present disclosure as apparent to those skilled in the art are intended to be included within the scope of the present disclosure

The invention claimed is:

1. A method of preparing a drug for treating a tumor, comprising mixing a compound with a structural formula as shown in Formula I and an EZH2 inhibitor with one or more pharmaceutically acceptable excipients, wherein the Formula I is given by:

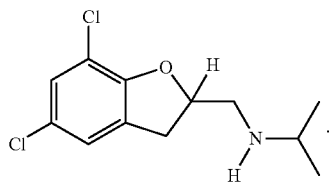

2. The method according to claim 1, wherein the EZH2 inhibitor is selected from DZNEP or EZH2 interfering RNA.

3. The method according to claim 1, wherein the tumor is selected from breast cancer, glioma, cervical cancer, gastric cancer, melanoma, lung cancer or liver cancer.

4. A composite formulation, wherein components of the composite formulation at least comprise a compound having a structural formula of Formula I and an EZH2 inhibitor, wherein the Formula I is given by:

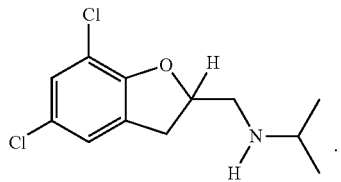 [SMILES: CC(C)NCC1Cc2cc(Cl)cc(Cl)c2O1]

5. The composite formulation according to claim 4, wherein the EZH2 inhibitor is selected from DZNEP or EZH2 interfering RNA.

6. The composite formulation according to claim 4, wherein a molar ratio of the compound having the structural formula of Formula I to the EZH2 inhibitor is (20-100):(100-10000).

7. The composite formulation according to claim 4, wherein a molar ratio of the compound having the structural formula of Formula I to the EZH2 inhibitor is (20-80):(100-10000), (20-40):(100-10000), (40-100):(100-10000), (40-80):(100-10000), (80-100):(100-10000), (20-100):(100-5000), (20-80):(100-5000), (20-40):(100-5000), (40-100):(100-5000), (40-80):(100-5000), (80-100):(100-5000), (20-100):(100-1000), (20-80):(100-1000), (20-40):(100-1000), (40-100):(100-1000), (40-80):(100-1000), (80-100):(100-1000), (20-100):(100-500), (20-100):(100-500), (20-80):(100-500), (20-40):(100-500), (40-100):(100-500), (40-80):(100-500), (80-100):(100-500), (20-100):(500-10000), (20-80):(500-10000), (20-40):(500-10000), (40-80):(500-10000), (20-100):(500-5000), (20-80):(500-5000), (20-40):(500-5000), (40-80):(500-5000), (80-100):(500-5000), (20-100):(1000-10000), (20-80):(1000-10000), (20-40):(1000-10000), (40-80):(1000-10000), (80-100):(1000-10000), (20-100):(1000-50000), (20-80):(1000-50000), (20-40):(1000-50000), (40-80):(1000-50000), (80-100):(1000-50000), (20-100):(5000-10000), (20-80):(5000-10000), (20-40):(5000-10000), (40-80):(5000-10000), (80-100):(5000-10000), (20-100):(500-1000), (20-80):(500-1000), (20-40):(500-1000), (40-80):(500-1000) or (80-100):(500-1000).

8. The composite formulation according to claim 4, wherein a molar ratio of the compound having the structural formula of Formula I to the EZH2 inhibitor is 20:100, 20:500, 20:1000, 20:5000, 20:10000, 40:100, 40:500, 40:1000, 40:5000, 40:10000, 80:100, 80:500, 80:1000, 80:5000, 80:10000, 100:100, 100:500, 100:1000, 100:5000 or 100:10000.

9. The composite formulation according to claim 4, wherein a molar ratio of the compound having the structural formula of Formula I to the EZH2 inhibitor is 40:1000.

10. A method of preparing a drug for treating a tumor, comprising mixing the components of the composite formulation according to claim 4 with one or more pharmaceutically acceptable excipients.

11. The method according to claim 10, wherein the tumor is selected from breast cancer, glioma, cervical cancer, gastric cancer, melanoma, lung cancer or liver cancer.

12. A method for treating a tumor, comprising the following operation: administering a pharmaceutically effective amount of a compound with a structural formula of Formula I to a subject, wherein the Formula I is given by:

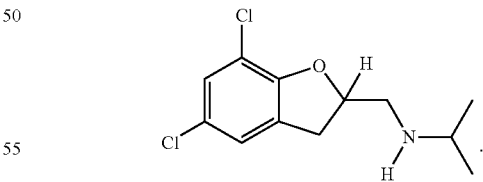

13. The method according to claim 12, wherein the tumor is selected from breast cancer, glioma, cervical cancer, gastric cancer, melanoma, lung cancer or liver cancer.

14. A method for treating a tumor, comprising the following operation: administering a pharmaceutically effective amount of a pharmaceutical composition to a subject, wherein effective components of the pharmaceutical composition include a compound with a structural formula of Formula I, wherein the Formula I is given by:

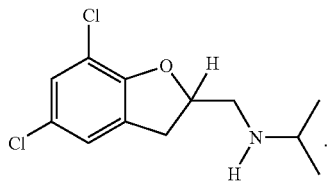 [SMILES: CC(C)NCC1Cc2cc(Cl)cc(Cl)c2O1]

15. The method according to claim 14, wherein the tumor is selected from breast cancer, glioma, cervical cancer, gastric cancer, melanoma, lung cancer or liver cancer.

16. A method for inhibiting tumor proliferation, tumor invasion and tumor metastasis, comprising the following operation: administering a pharmaceutically effective amount of a compound with a structural formula of Formula I to a subject, wherein the Formula I is given by:

17. The method according to claim 16, wherein the tumor is selected from breast cancer, glioma, cervical cancer, gastric cancer, melanoma, lung cancer or liver cancer.

18. A method for inhibiting tumor proliferation, tumor invasion and tumor metastasis, comprising the following operation: administering a pharmaceutically effective amount of a pharmaceutical composition to a subject, wherein effective components of the pharmaceutical composition include a compound with a structural formula of Formula I, wherein the Formula I is given by:

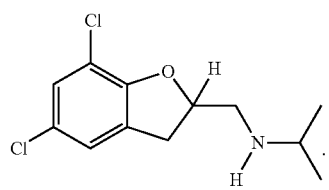 [SMILES: CC(C)NCC1Cc2cc(Cl)cc(Cl)c2O1]

19. The method according to claim 18, wherein the tumor is selected from breast cancer, glioma, cervical cancer, gastric cancer, melanoma, lung cancer or liver cancer.

20. A method for treating a tumor, comprising the following operation: administering a pharmaceutically effective amount of a compound with a structural formula of Formula I and an EZH2 inhibitor to a subject, wherein the Formula I is given by:

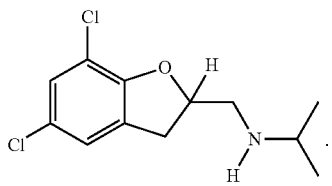 [SMILES: CC(C)NCC1Cc2cc(Cl)cc(Cl)c2O1]

21. The method according to claim 20, wherein the EZH2 inhibitor is selected from DZNEP or EZH2 interfering RNA.

22. The method according to claim 20, wherein the tumor is selected from breast cancer, glioma, cervical cancer, gastric cancer, melanoma, lung cancer or liver cancer.

23. The method according to claim 20, wherein a molar ratio of the compound having the structural formula of Formula I to the EZH2 inhibitor is (20-100):(100-10000).

24. The method according to claim 20, wherein a molar ratio of the compound having the structural formula of Formula I to the EZH2 inhibitor is (20-80):(100-10000), (20-40):(100-10000), (40-100):(100-10000), (40-80):(100-10000), (80-100):(100-10000), (20-100):(100-5000), (20-80):(100-5000), (20-40):(100-5000), (40-100):(100-5000), (40-80):(100-5000), (80-100):(100-5000), (20-100):(100-1000), (20-80):(100-1000), (20-40):(100-1000), (40-100):(100-1000), (40-80):(100-1000), (80-100):(100-1000), (20-100):(100-500), (20-100):(100-500), (20-80):(100-500), (20-40):(100-500), (40-100):(100-500), (40-80):(100-500), (80-100):(100-500), (20-100):(500-10000), (20-80):(500-10000), (20-40):(500-10000), (40-80):(500-10000), (20-100):(500-5000), (20-80):(500-5000), (20-40):(500-5000), (40-80):(500-5000), (80-100):(500-5000), (20-100):(1000-10000), (20-80):(1000-10000), (20-40):(1000-10000), (40-80):(1000-10000), (80-100):(1000-10000), (20-100):(1000-50000), (20-80):(1000-50000), (20-40):(1000-50000), (40-80):(1000-50000), (80-100):(1000-50000), (20-100):(5000-10000), (20-80):(5000-10000), (20-40):(5000-10000), (40-80):(5000-10000), (80-100):(5000-10000), (20-100):(500-1000), (20-80):(500-1000), (20-40):(500-1000), (40-80):(500-1000) or (80-100):(500-1000).

25. The method according to claim 20, wherein a molar ratio of the compound having the structural formula of Formula I to the EZH2 inhibitor is 20:100, 20:500, 20:1000, 20:5000, 20:10000, 40:100, 40:500, 40:1000, 40:5000, 40:10000, 80:100, 80:500, 80:1000, 80:5000, 80:10000, 100:100, 100:500, 100:1000, 100:5000 or 100:10000.

26. The method according to claim 20, wherein a molar ratio of the compound having the structural formula of Formula I to the EZH2 inhibitor is 40:1000.

27. The method according to claim 14, wherein the pharmaceutical composition is administered to a patient in need of treatment by oral administration, injection, sublingual administration, rectal administration, vaginal administration, transdermal administration or spray inhalation.

28. The method according to claim 14, wherein a dosage form of the pharmaceutical composition is tablet, granule, capsule, pill, dropping pill, powder, lotion, syrup, stomach plate, mixture, medicinal liquor, tincture, buccal tablet, liquid extract and extract, paste, gel, ointment, medicinal tea, lotion, coating agent, liniment, aerosol or spray.

29. A method for treating a tumor, comprising the following operation: administering a pharmaceutically effective amount of a pharmaceutical composition to a subject, wherein effective components of the pharmaceutical composition include a compound with a structural formula of Formula I and an EZH2 inhibitor, wherein the Formula I is given by:

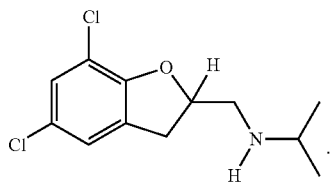 [SMILES: CC(C)NCC1Cc2cc(Cl)cc(Cl)c2O1]

30. The method according to claim 29, wherein the EZH2 inhibitor is selected from DZNEP or EZH2 interfering RNA.

31. The method according to claim 29, wherein the tumor is selected from breast cancer, glioma, cervical cancer, gastric cancer, melanoma, lung cancer or liver cancer.

32. The method according to claim 29, wherein a molar ratio of the compound having the structural formula of Formula I to the EZH2 inhibitor is (20-100):(100-10000).

33. The method according to claim 29, wherein a molar ratio of the compound having the structural formula of Formula I to the EZH2 inhibitor is (20-80):(100-10000), (20-40):(100-10000), (40-100):(100-10000), (40-80):(100-10000), (80-100):(100-10000), (20-100):(100-5000), (20-80):(100-5000), (20-40):(100-5000), (40-100):(100-5000), (40-80):(100-5000), (80-100):(100-5000), (20-100):(100-1000), (20-80):(100-1000), (20-40):(100-1000), (40-100):(100-1000), (40-80):(100-1000), (80-100):(100-1000), (20-100):(100-500), (20-100):(100-500), (20-80):(100-500), (20-40):(100-500), (40-100):(100-500), (40-80):(100-500), (80-100):(100-500), (20-100):(500-10000), (20-80):(500-10000), (20-40):(500-10000), (40-80):(500-10000), (20-100):(500-5000), (20-80):(500-5000), (20-40):(500-5000), (40-80):(500-5000), (80-100):(500-5000), (20-100):(1000-10000), (20-80):(1000-10000), (20-40):(1000-10000), (40-80):(1000-10000), (80-100):(1000-10000), (20-100):(1000-50000), (20-80):(1000-50000), (20-40):(1000-50000), (40-80):(1000-50000), (80-100):(1000-50000), (20-100):(5000-10000), (20-80):(5000-10000), (20-40):(5000-10000), (40-80):(5000-10000), (80-100):(5000-10000), (20-100):(500-1000), (20-80):(500-1000), (20-40):(500-1000), (40-80):(500-1000) or (80-100):(500-1000).

34. The method according to claim 29, wherein a molar ratio of the compound having the structural formula of Formula I to the EZH2 inhibitor is 20:100, 20:500, 20:1000, 20:5000, 20:10000, 40:100, 40:500, 40:1000, 40:5000, 40:10000, 80:100, 80:500, 80:1000, 80:5000, 80:10000, 100:100, 100:500, 100:1000, 100:5000 or 100:10000.

35. The method according to claim 29, wherein a molar ratio of the compound having the structural formula of Formula I to the EZH2 inhibitor is 40:1000.

36. The method according to claim 29, wherein the pharmaceutical composition is administered to a patient in need of treatment by oral administration, injection, sublingual administration, rectal administration, vaginal administration, transdermal administration or spray inhalation.

37. The method according to claim 29, wherein a dosage form of the pharmaceutical composition is tablet, granule, capsule, pill, dropping pill, powder, lotion, syrup, stomach plate, mixture, medicinal liquor, tincture, buccal tablet, liquid extract and extract, paste, gel, ointment, medicinal tea, lotion, coating agent, liniment, aerosol or spray.

* * * * *